(12) United States Patent
Yamamoto

(10) Patent No.: US 7,658,927 B2
(45) Date of Patent: Feb. 9, 2010

(54) MATERIALS AND METHODS FOR IMMUNIZING AGAINST FIV INFECTION

(75) Inventor: Janet K. Yamamoto, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 10 days.

(21) Appl. No.: 11/326,062

(22) Filed: Jan. 5, 2006

(65) Prior Publication Data

US 2006/0147467 A1 Jul. 6, 2006

Related U.S. Application Data

(63) Continuation-in-part of application No. 10/844,658, filed on May 12, 2004.

(60) Provisional application No. 60/470,066, filed on May 12, 2003.

(51) Int. Cl.
A61K 39/00 (2006.01)
(52) U.S. Cl. .................................. 424/184.1
(58) Field of Classification Search ............... None
See application file for complete search history.

(56) References Cited

U.S. PATENT DOCUMENTS

| | | | |
|---|---|---|---|
| 4,861,720 | A | 8/1989 | Pedersen et al. |
| 5,037,753 | A | 8/1991 | Pedersen et al. |
| 5,118,602 | A | 6/1992 | Pedersen et al. |
| 5,275,813 | A | 1/1994 | Yamamoto et al. |
| 5,401,628 | A | 3/1995 | Chiodi |
| 5,510,106 | A | 4/1996 | Yamamoto et al. |
| 5,530,101 | A | 6/1996 | Queen et al. |
| 5,565,319 | A | 10/1996 | Pedersen et al. |
| 5,585,089 | A | 12/1996 | Queen et al. |
| 5,693,762 | A | 12/1997 | Queen et al. |
| 5,700,469 | A | 12/1997 | McMichael et al. |
| 5,763,160 | A | 6/1998 | Wang |
| 5,846,546 | A | 12/1998 | Hurwitz et al. |
| 5,846,825 | A | 12/1998 | Yamamoto |
| 5,849,533 | A | 12/1998 | Berman et al. |
| 6,107,077 | A | 8/2000 | Yamamoto |
| 6,180,370 | B1 | 1/2001 | Queen et al. |
| 6,254,872 | B1 | 7/2001 | Yamamoto |
| 6,407,213 | B1 | 6/2002 | Carter et al. |
| 6,447,993 | B1 | 9/2002 | Yamamoto |
| 6,500,623 | B1 | 12/2002 | Tung |
| 6,503,753 | B1 | 1/2003 | Rios |
| 6,544,528 | B1 | 4/2003 | Yamamoto |
| 2001/0004531 | A1 | 6/2001 | Sung et al. |
| 2002/0032165 | A1 | 3/2002 | Johnson et al. |
| 2002/0156037 | A1 | 10/2002 | Volkin et al. |
| 2003/0104611 | A1 | 6/2003 | Johnston et al. |
| 2003/0223964 | A1 | 12/2003 | Barnett et al. |
| 2004/0009941 | A1 | 1/2004 | Johnson et al. |
| 2004/0047878 | A1 | 3/2004 | Deng et al. |
| 2004/0076632 | A1 | 4/2004 | Deng et al. |
| 2005/0031639 | A1 | 2/2005 | Yamamoto |

FOREIGN PATENT DOCUMENTS

| | | |
|---|---|---|
| WO | WO 93/01278 | 1/1993 |
| WO | WO 94/20622 | 9/1994 |
| WO | WO 9428929 A1 | 12/1994 |
| WO | WO 96/30045 | 10/1996 |
| WO | WO 02/067984 A2 | 9/2002 |

OTHER PUBLICATIONS

Elyar et al., Perspectives on FIV vaccine development, Vaccine, 1997, 15(12/13):1437-1444.*

Abimiku, A.G., et al. "HIV-1 recombinant poxvirus vaccine induces cross-protection against HIV-2 challenge in rhesus macaques," *Nat. Med.*, 1995, pp. 321-329, vol. 1.

Ackley, C. et al. "Immunologic Abnormalities in Pathogen-Free Cats Experimentally Infected with Feline Immunodeficiency Virus" *Journal of Virology*, Nov. 1990, pp. 5652-5655, vol. 64, No. 11.

Altschul, S.F. et al. "Gapped BLAST and PSI-BLAST: A New Generation of Protein Database Search Programs," *Nucl. Acids Res.*, 1997, pp. 3389-3402, vol. 25, No. 17.

Bottiger, B., et al. "Envelope cross-reactivity between human immunodeficiency virus type 1 and 2 detected by different serological methods: correlation between cross-neutralization and reactivity against the main neutralizing site," *J. Virol.*, 1990, pp. 3492-3499, vol. 64, No. 7.

Byars, N.E. et al. "Adjuvant formulation for use in vaccines to elicit both cell-mediated and humoral immunity" *Vaccine*, Sep. 1987, pp. 223-228, vol. 5.

(Continued)

Primary Examiner—Robert B Mondesi
Assistant Examiner—Nicole Kinsey White
(74) Attorney, Agent, or Firm—Saliwanchik, Lloyd & Saliwanchik

(57) ABSTRACT

The subject invention pertains to methods and compositions for protecting feline animals from infection by FIV using immunogens derived from primate immunodeficiency viruses, including HIV and SIV. Methods for vaccinating feline animals with the subject vaccine compositions are described. Feline animals vaccinated according to the methods and compositions of the subject invention exhibit protective humoral and cellular immune responses to FIV when challenged with FIV. The subject invention further concerns methods and compositions for protecting humans and other animals against infection by immunodeficiency viruses, such as HIV and FIV.

Figure 1A:
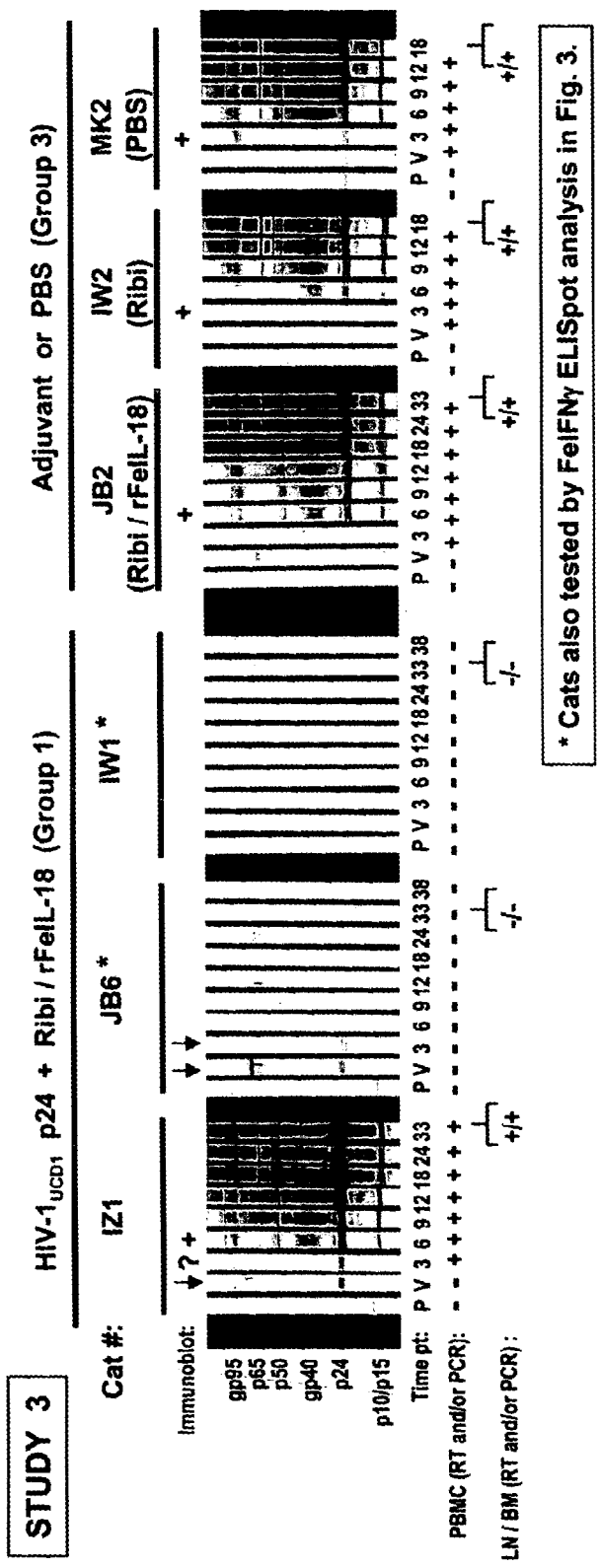

10 Claims, 6 Drawing Sheets
(1 of 6 Drawing Sheet(s) Filed in Color)

OTHER PUBLICATIONS

Calarota, S.A., et al. "Present status of human HIV vaccine development," "AIDS", 2003, pp. S73-S84, vol. 17, Supp. 4.

Cohen, J. "Vaccine results lose significance under scrutiny," Science, 2003, p. 1495, vol. 299.

De Ronde, A. et al. "Antibody Response in Cats to the Envelope Proteins of Feline Immunodeficiency Virus: Identification of an Immunodominant Neutralization Domain" Virology, 1994, pp. 257-264, vol. 198.

Felgner, P. et al. "Lipofection: A highly efficient, lipid-medicated DNA-transfection procedure" Proc. Natl. Acad. Sci. USA, Nov. 1987, pp. 7413-7417, vol. 84.

Gaucher, D., et al. "Gerbil interleukin-18 and caspase-1: cloning, expression and characterization," Gene, 2003, pp. 159-166, vol. 307.

Greenberg, A.E., et al. "HIV-2 and natural protection against HIV-1 infection," Science, 1996, pp. 1959-1960, vol. 272.

Guyader, M., et al. "Genome organization and transactivation of the human immunodeficiency virus type 2," Nature, 1987, pp. 662-669, vol. 326.

Henderson, D.A., et al. "Smallpox and vaccinia," In: Vaccines, 3rd Ed., 2004, pp. 123-153, Plotkin SA, Orenstein WA (editors). Elsevier Inc., Philadelphia.

Hosie, M. J. et al. "Protection against Homologous but Not Heterologous Challenge Induced by Inactivated Feline Immunodeficiency Virus Vaccines" Journal of Virology, 1995, vol. 69, No. 2, pp. 1253-1255.

Hosie, M. et al. "Serological responses of cats to feline immunodeficiency virus" AIDS, 1990, pp. 215-220, vol. 4.

Ishizaka, T., A. et al. "Molecular cloning of feline interferon-γ-inducing factor (interleukin-18) and its expression in various tissues," Vet. Immunol. Immunopathol., 2001, pp. 209-218, vol. 79.

Johnson, C. M. et al. "FIV as a Model for AIDS Vaccination" AIDS Research and Human Retroviruses, 1994, vol. 10, No. 3, pp. 225-228.

Kakinuma, S. et al. "Nucleotide Sequence of Feline Immunodeficiency Virus: Classification of Japanese Isolates into Two Subtypes Which Are Distinct from Non-Japanese Subtypes" Journal of Virology, Jun. 1995, pp. 3639-3646, vol. 69, No. 6.

Karlin, S. et al. "Methods for Assessing the Statistical Significance of Molecular Sequence Features by Using General Scoring Schemes," Proc. Natl. Acad. Sci. USA, 1990, pp. 2264-2268, vol. 87.

Karlin, S. et al. "Applications and Statistics for Multiple High-Scoring Segments in Molecular Sequences," Proc. Natl. Acad. Sci. USA, 1993, pp. 5873-5877, vol. 90.

Lerner, D.L., et al. "Felis catus interleukin-4 mRNA," NCBI GenBank, 1997 (accession U39634).

Leutenegger, C. M. et al. "Immunization of Cats against Feline Immunodeficiency Virus (FIV) Infection by Using Minimalistic Immunogenic Defined Gene Expression Vector Vaccines Expressing FIV gp140 Alone or with Feline Interleukin-12 (IL-12), IL-16, or a CpG Motif" Journal of Virology, Nov. 2000, pp. 10447-10457, vol. 74, No. 22.

Louwagie, J. et al. "Phylogenetic analysis of gag genes from 70 international HIV-1 isolates provides evidence for multiple genotypes" AIDS, 1993, pp. 769-780, vol. 7, No. 6.

Matsuo, K., et al., "Highly conserved epitope domain in major core protein p24 is structurally similar among human, simian and feline immunodeficiency viruses," J. Gen. Virol., 1992, pp. 2445-2450, vol. 73.

McMichael, A.J., et al. "HIV vaccines 1983-2003," Nat. Med., 2003. pp. 874-880, vol. 9.

Merrifield, R. B. "Solid Phase Peptide Synthesis. I. The Synthesis of a Tetrapeptide" Amer. Chem. Soc., Jul. 20, 1963, pp. 2149-2156, vol. 85.

Murphy, F. et al. "Virus Taxonomy" Fields Virology, 1990, pp. 9-36, Chapter 2, $2^{nd}$ edition, Raven Press, Ltd., New York.

Murphy, F.A. "Virus Taxonomy," In: Fundamental Virology, 3rd Ed., 1996, pp. 15-57, Fields BN, Knipe DM, PM Howley PM (editors). Lippincott, Raven Publishers, Philadelphia.

Nath, M.D., et al. "In vitro assembly of feline immunodeficiency virus capsid protein: biological role of conserved cysteines," Arch. Biochem. Biophys., 2001, pp. 287-294, vol. 392.

Nixon, D.F., et al. "An HIV-1 and HIV-2 cross-reactive cytotoxic T-cell epitope," AIDS, 1990, pp. 841-845, vol. 4.

Norrgren, H., et al. "Trends and interaction of HIV-1 and HIV-2 in Guinea-Bissau, West Africa: no protection of HIV-2 against HIV-1 infection," AIDS, 1999, pp. 701-707, vol. 13.

Okada, S. et al. "Superinfection of Cats with Feline Immunodeficiency Virus Subtypes A and B" AIDS Research and Human Retroviruses, 1994, vol. 10, No. 12, pp. 1739-1746.

Olmsted, R. et al. "Molecular cloning of feline immunodeficiency virus" Proc. Natl. Acad. Sci. USA, Apr. 1989, pp. 2448-2452, vol. 86.

Olmsted, R. et al. "Nucleotide sequence analysis of feline immunodeficiency virus: Genome organization and relationship to other lentiviruses" Pro. Natl. Acad. Sci. USA, Oct. 1989, pp. 8088-8092, vol. 86.

Pedersen, N. et al. "Isolation of a T-Lymphotropic Virus from Domestic Cats with an Immunodeficiency-Like Syndrome" Science, Feb. 13, 1987, pp. 790-793, vol. 235.

Posnett, D. et al. "A Novel Method for Producing Anti-peptide Antibodies" The Journal of Biological Chemistry, Feb. 5, 1988, pp. 1719-1725, vol. 263, No. 4.

Pu R., et al. "Dual-subtype FIV vaccine (Fel-O-Vax® FIV) protection against heterologous subtype B FIV isolate," Journal of Feline Medicine & Surgery, 2005, pp. 65-70, vol. 7, No. 1.

Pu, R., et al. "FIV antigens induce potent cross-reactive immunity to HIV-1," Experimental Biology 2002. New Orleans, Apr. 2002 [FASEB Journal, p. A298, Abstract No. 237.21].

Pu, R. et al. "Dual-subtype FIV vaccine protects cats against in vivo swarms of both homologous and heterologous subtype FIV isolates" AIDS, 2001, pp. 1225-1237, vol. 15.

Reis E Sousa, C. "Toll-like receptors and dendrite cells: for whom the bug tolls," Semin. Immunol., 2004, pp. 27-34, vol. 16.

Rigby, M. A. et al. "Evolution of structural proteins of feline immunodeficiency virus: molecular epidemiology and evidence of selection for change" Journal of General Virology, 1993, pp. 425-436, vol. 74.

Robert-Guroff, M., et al. "Cross-neutralization of human immunodeficiency virus type 1 and 2 and simian immunodeficiency virus isolates," J. Virol., 1992, pp. 3602-3608, vol. 66, No. 6.

Rowland-Jones, S., et al. "HIV-specific cytotoxic T-cells in HIV-exposed but uninfected Gambian women," Nat. Med., 1995, pp. 59-64, vol. 1, No. 1.

Salek-Ardakani, S., et al. (2002) "High level expression and purification of the Epstein-Barr virus encoded cytokine viral interleukin 10: efficient removal of endotoxin," Cytokine, 2002, pp. 1-13, vol. 17, No. 1.

Sodora, D. et al. "Identification of Three Feline Immunodeficiency Virus (FIV) env Gene Subtypes and Comparison of the FIV and Human Immunodeficiency Virus Type 1 Evolutionary Patterns" Journal of Virology, Apr. 1994, pp. 2230-2238, vol. 68, No. 4.

Talbott, R. L. et al. "Nucleotide sequence and genomic organization of feline immunodeficiency virus" Proc. Natl. Acad. Sci. USA, Aug. 1989, pp. 5743-5747, vol. 86.

Tam, J. "Synthetic peptide vaccine design: Synthesis and properties of a high-density multiple antigenic peptide system" Proc. Natl. Acad. Sci. USA, Aug. 1988, pp. 5409-5413, vol. 85.

Tanabe, T., et al. "Feline immunodeficiency virus lacks sensitivity to the antiviral activity of feline IFNγ" J. Interferon Cytokine Res., 2001, pp. 1039-1046, vol. 21.

Travers, K., et al. "Natural protection against HIV-1 infection provided by HIV-2," Science, Jun. 16, 1995, pp. 1612-1615, vol. 268.

Uhl, E.W., et al. "FIV vaccine development and its importance to veterinary and human medicine: a review," Vet. Immunol. Immunopath., 2002, pp. 113-132, vol. 90.

Schim Van Der Loeff, M.F, et al. "HIV-2 infection does not protect against HIV-1 infection in a rural community in Guinea-Bissau," AIDS, 2001, pp. 2303-2310, vol. 15.

Weigel, B.J., et al. "Comparative analysis of murine marrow-derived dendritic cells generated by Flt3L or GM-CSF/IL-4 and matured with immune stimulatory agents on the in vivo induction of antileukemia responses," Blood, Dec. 1, 2002, pp. 4169-4176, vol. 100, No. 12.

Whetter, L. et al. "Pathogenesis of simian immunodeficiency virus infection" Journal of General Virology, 1999, pp. 1557-1568, vol. 80.

Wondimu, A., et al. "Molecular cloning, expression and characterization of the *Canis familiaris* interleukin-4," *Cytokine*, Nov. 7, 2001, pp. 88-92, vol. 16, No. 3.

Yamamoto, J.K., B.A. Torres, R. Pu (2002) "Development of the dual-subtype FIV vaccine," *AIDScience* Apr. 2002, 2(8), website at aidscience.org/Articles/AIDScience020.asp/ Accessed Dec. 25, 2004.

Yamamoto, J. et al. "Feline Immunodeficiency Syndrome-A Comparison between Feline T-Lymphotropic Lentivirus and Feline Leukemia Virus" *Leukemia*, 1988, pp. 204S-215S, vol. 2, No. 12 Supplement.

Yamamoto, J. et al. "Pathogenesis of experimentally induced feline immunodeficiency virus infection in cats" *American Journal of Veterinary Research*, Aug. 1988, pp. 1246-1258, vol. 49, No. 8.

Yamamoto, J.K., et al. "Experimental vaccine protection against homologous and heterologous strains of feline immunodeficiency virus," *J. Virol.*, 1993, pp. 601-605, vol. 67.

Satoshi, N. et al. "Establishment of FIV-Producing Cell Lines From FIV Seropositive Cats" V International Conference on AIDS, The Scientific and Social Challenge, 1989, XP-000972975, abstract only, p. 598.

Yamamoto, J. K. et al. "Experimental Vaccine Protection Against Feline Immunodeficiency Virus" *AIDS Research and Human Retroviruses*, 1991, vol. 7, No. 11, pp. 911-922.

Yamamoto, J. K. et al. "Development of IL-2-Independent Feline Lymphoid Cell Lines Chronically Infected with Feline Immunodeficiency Virus: Importance for Diagnostic Reagents and Vaccines" *Intervirology*, 1991, vol. 32, pp. 361-375.

De Rozieres, S. et al. "Characterization of a Highly Pathogenic Molecular Clone of Feline Immunodeficiency Virus Clade C" *Journal of Virology*, 2004, vol. 78, No. 17, pp. 8971-8982.

Yazbak, F.E., et al. "Postpartum live virus vaccination: lessons from veterinary medicine," *Med. Hypoth.*, 2002, pp. 280-282, vol. 59.

Zvelebil, M.J., et al. "Predictions of linear T-cell and B-cell epitopes in proteins encoded by HIV-1, HIV-2 and $SIV_{MAC}$ and the conservation of these sites between strains," *FEBS Lett*, Dec. 1988, pp. 9-21, vol. 242.

Coleman, J.K., et al. "HIV-1 p. 24 Vaccine Protects Cats Against Feline Immunodeficiency Virus Infection," *AIDS*, 2005, pp. 1457-1466, vol. 19.

Dunham, S.P. "Lessons from the cat: development of vaccines against lentiviruses" *Veterinary Immunology and Immunopathology*, 2006, pp. 67-77, vol. 112.

Flynn, J.N. et al. "Induction of feline immunodeficiency virus-specific cytotoxic T cells in vivo with carrier-free synthetic peptide" *Journal of Virology*, Sep. 1994, pp. 5835-5844, vol. 68, No. 9.

Nixon, D.F. et al. "HIV-1 gag-specific cytotoxic T lymphocytes defined with recombinant vaccinia virus and synthetic peptides" *Nature*, Dec. 1988, pp. 484-487, vol. 336.

Sjolander, S. et al. "Induction of homologous virus neutralizing antibodies in guinea-pigs immunized with two human immunodeficiency virus type 1 glycoprotein gp 120-iscom preparations" *Vaccine*, 1996, pp. 344-352, vol. 14, No. 4.

Tijhaar, E.J. et al. "*Salmonella typhimurium* aroA recombinants and immune-stimulating complexes as vaccine candidates for feline immunodeficiency virus" *Journal of General Virology*, 1997, pp. 3265-3275, vol. 78.

* cited by examiner

FIG. 2A

MATERIALS AND METHODS FOR IMMUNIZING AGAINST FIV INFECTION

CROSS REFERENCE TO RELATED APPLICATIONS

This application is a continuation-in-part of U.S. application Ser. No. 10/844,658, filed May 12, 2004, which claims the benefit of U.S. Provisional Application Ser. No. 60/470,066, filed May 12, 2003, each of which are hereby incorporated by reference in its entirety, including all figures, nucleic acid sequences, amino acid sequences, and tables.

The subject invention was made with government support under a research project supported by National Institutes of Health Grant No. NIH AI30904. The government has certain rights in this invention.

BACKGROUND OF THE INVENTION

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4:CD8 cell ratio and, in some cases, an increase in CD8-bearing lymphocytes. Based on molecular, biochemical and immunopathologic characteristics, FIV infection of cats is now considered to be a better feline AIDS model than FeLV-FAIDS.

Cloning and sequence analysis of FIV has been reported in Olmsted et al. (1989a); Olmsted et al. (1989b); and Talbott et al. (1989). Hosie and Jarrett (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al., 1994; Rigby et al., 1993; and Louwagie et al., 1993), little is known about the correlation between the genotype and immunotype of subtypes. FIV viral isolates have been classified into four FIV subtypes: A, B, C and D. (Kakinuma et al., 1995). Infectious isolates and infectious molecular clones have been described for all FIV subtypes except for subtype C (Sodora et al., 1994). Subtype C FIV has originally been identified from cellular DNA of cats from Canada (Sodora et al., 1994; Rigby et al., 1993; Kakinuma et al., 1995). FIV strains identified in the art include (subtype of the strain is shown in parenthesis) Petaluma (A), Dixon (A), UK8 (A), Dutch113 (A), Dutch19K (A), UK2 (A), SwissZ2 (A), Sendai-1 (A), USCAzepy01A (A), USCAhnky11A (A), USCAtt-10A (A), USCAlemy01 (A), USCAsam-01A (A), PPR (A), FranceWo, Netherlands, Bangston (A/B), Aomori-1 (B), Aomori-2 (B), USILbrny03B (B), TM2 (B), Sendai-2 (B), USCKlgri02B (B), Yokohama (B), USMAsboy03B (B), USTXmtex03B (B), USMCglwd03B (B), CABCpbar03C (C), CABCpbar07C (C), CABCpady02C (C), Shizuoka (D), and Fukuoka (D).

Although major strides have been made with antiviral drug therapy, the development of an effective vaccine against HIV-1 is still considered central to the control of the AIDS epidemic (Calarota et al., 2003). Multiple HIV vaccine designs using different HIV-1 strains are currently in various phases of clinical trials (Calarota et al., 2003; Cohen, 2003; IAVI Report. Ongoing trials of preventive HIV vaccines (last updated: Dec. 14, 2004). IAVI Report Online Special Features: www.iavireport.org/specials/OngoingTrialsofPreventiveHIVVaccines.pdf). Even in light of these clinical trials, it is still unclear what HIV-1 epitopes and immune mechanisms are essential for vaccine protection (Calarota et al., 2003; McMichael et al., 2003). Similar issues were faced during the development of an FIV vaccine for domestic cats (Uhl et al., 2002). As a means to broaden FIV vaccine efficacy, a dual-subtype vaccine was developed using FIV strains from long-term nonprogressor cats (Uhl et al., 2002; Yamamoto et al., 2002). This vaccine demonstrated moderate to significant protection of cats against both homologous and heterologous FIV challenges (Uhl et al., 2002; Yamamoto et al., 2002, Pu et al., 2001; Pu et al., 2005). Furthermore, this vaccine induced not only broad neutralizing antibodies (Pu et al., 2001) but antibodies cross-reactive to HIV-1 proteins, especially to HIV-1 core protein (p24) and group-specific antigens (Gag) (Pu et al., 2002). The FIV epitopes responsible for providing the dual-subtype vaccine protection have yet to be determined.

Gag and other antigens conserved among viruses from the same subfamily frequently induce antibodies that cross-react with other subfamily members (Pu et al., 2002; Matsuo et al., 1992; Nath et al., 2001; Zvelebil et al., 1988; Murphy, 1996). Some cross-reactive antigens have been used as immunogens for vaccine against viruses from the same subfamily (Henderson et al., 2004; Yazbak et al., 2002). Classic examples of such vaccines are the use of vaccinia virus vaccines for smallpox in humans and human measles vaccines for canine distemper in puppies (Henderson et al., 2004; Yazbak et al., 2002). Consequently, protective vaccines based on cross-reactive antigens have been shown to provide broad immunity, and may be useful against viruses that are currently evolving in a new host, such as HIV infection of humans.

Although cross-protection against HIV-1 with prior HIV-2 infection has been reported in multiple retrospective studies (Travers et al., 1995; Greenberg et al., 1996), controversy still exists with multiple studies reporting no protection (Norrgren et al., 1999; Schim van der Loeff et al., 2001). Even though amino acid (aa) sequences of the structural gene products exhibit only limited identity (<60%) between HIV-1 and HIV-2 (Guyader et al., 1987), some of the cross-reactive epitopes between these two major HIV groups have been reported to induce cross-neutralizing antibodies and cross-reactive cytotoxic T lymphocyte (CTL) activities (Robert-Guroff et al., 1992; Bottiger et al., 1990; Nixon et al., 1990; Rowland-Jones et al., 1995). Moreover, poxvirus-vectored recombinant HIV-1 vaccine priming followed by HIV-2 protein boost, conferred cross-protection against HIV-2 challenge in macaques (Abimiku et al., 1995). However, cross-reactive antigen-induced protective immunity has not been reported against distinct heterologous-species viruses (HIV-1 and FIV).

BRIEF SUMMARY OF THE INVENTION

The subject invention pertains to methods and compositions for protecting feline animals from infection by FIV using immunogens derived from primate immunodeficiency viruses, including HIV and SIV. Methods and compositions for vaccinating feline animals with the subject vaccine compositions are described. Feline animals vaccinated according to the methods and compositions of the subject invention exhibit protective immune responses to FIV when challenged with FIV.

The subject invention also concerns methods for selecting for epitopes that are evolutionarily conserved among immunodeficiency viruses. Evolutionarily conserved epitopes of immunodeficiency viruses identified using methods of the present invention also constitute part of the invention. The subject invention further concerns methods and compositions for protecting humans and other animals against infection by immunodeficiency viruses, such as HIV and FIV.

BRIEF DESCRIPTION OF THE DRAWINGS

The file of this patent contains at least one drawing executed in color. Copies of this patent with the color drawing will be provided by the Patent and Trademark Office upon request and payment of the necessary fee.

FIGS. 1A and 1B show the kinetics of FIV antibody development and FIV infection. FIV antibody profile and FIV infection results of all HIV-1 p24-vaccinated cats in Group 1 (Studies 3 and 4) and select adjuvant-immunized and PBS-immunized cats (Group 3, Study 3; Group 2, Study 4) are shown. The results for Study 3 are shown in FIG. 1A and the results for Study 4 are shown in FIG. 1B. The time points (Time pt) tested for immunoblot antibodies and virus isolation of PBMC are pre-vaccination (P), 3 weeks post-3rd immunization (before challenge) (V), and after challenge on 3, 6, 9, 12, 18, 24, 33, 34, and 38 wpi (select post-challenge results shown). The antibodies reactive to FIV p24 induced by HIV-1 p24 vaccination are presented with an arrow above the appropriate immunoblot strip. The first time point of the infecton-induced FIV-antibody detection is shown as either weak (±) or definite positive (+) above the corresponding immunoblot strip. Those antibodies to FIV p24 that are potentially induced by both HIV-1 vaccination and FIV infection are shown with a question mark (?) above the immunoblot strip. Cat #MG1 (Study 4) after 3rd vaccination before challenge was positive for FIV p24 antibodies by immunoblot analysis at only 1:50 dilution, while cats #IW1 (Study 3) and #AA1 (Study 4) after 3rd vaccination before challenge were negative for FIV antibodies by both immunoblot analysis (1:50 dilution) and ELISA (1:200 dilution).

The FIV infection results from PBMC based on RT activity (RT) and/or proviral PCR (PCR) are shown with either positive (+) or negative (–) immediately below the corresponding time points. The RT/PCR results for LN and BM cells are shown on the row designated as LN/BM with the first result (+/ or –/) for LN cells and the second result (/+ or /–) for BM cells. All vaccinated/unprotected cats (#IZ1, [two cats not shown], Study 3; #AA1, Study 4) and all adjuvant-immunized and PBS-immunized control cats (#JB2, #IW2, #MK2, [three cats not shown], Study 3; #MD3, #MG4, #MK4, Study 4) after challenge were positive FIV infection by 3-12 wpi in virus isolation/PCR analyses and by 3-15 wpi in immunoblot analysis (immunoblots of 15 wpi not shown). The earliest time points of virus detection in challenged control cats were 3 wpi for Study 3 ($FIV_{Bang}$) and 6 wpi for Study 4 ($FIV_{FC1}$), which were identical to the earliest time points of FIV antibody detection in these cats by immunoblot analysis. Based on the infected-control-cat results, none of the vaccinated/unprotected cats in Studies 3 (#IZ1, two other cats not shown) and 4 (#AA1) had enhancement in FIV infection.

FIGS. 2A and 2B show FIV p24 immunoblot analysis of HIV-1 p24-vaccinated-cat sera (FIG. 2A), aa sequence alignment of HIV-1 and FIV strains used (FIG. 2B), and T-cell/B-cell peptide sequence alignment (FIG. 2B). The sera (1:100 dilution) from three $HIV\text{-}1_{LAI/LAV}$ p24- and two $HIV\text{-}1_{UCD1}$ p24-vaccinated cats before vaccination (Pr) and three weeks after each vaccination (V1, post-1st vaccination; V2, post-2nd vaccination; V3, post-3rd vaccination before challenge) were evaluated by immunoblot analysis (Pu et al., 2001) using recombinant $FIV_{Bang}$ p24 as antigenic substrate (0.2 μg/strip) (FIG. 2A). Three of the five cats shown were vaccinated with $HIV\text{-}1_{LAI/LAV}$ in Ribi/rHuIL-12 (#ID4 and #626, Study2; #R99, Study 1) and remaining two cats were vaccinated with $HIV\text{-}1_{UCD1}$ p24 in Ribi/rHuIL-12 (#G9F, Study 1; #JB6, Study 3). The earliest time point of positive antibody detection in FIV p24 immunoblot analysis was after the $2^{nd}$ vaccination (#626 strong reactivity, #ID4 weak reactivity).

Sequence homology analysis between $HIV\text{-}1_{UCD1}$ and $FIV_{Bang}$ is shown with (.) for aa homology and (:) for aa identity according to the GeneStream Align program (GeneStream Align program. http://xylian.igh.cnrs.fr/) (FIG. 2B). Only aa residues that are different from $HIV\text{-}1_{UCD1}$ and $FIV_{Bang}$ are shown for $HIV\text{-}1_{LAI/LAV}$ (above $HIV\text{-}1_{UCD1}$ sequence) and $FIV_{FC1}$ (below $FIV_{Bang}$ sequence), respectively. In addition, the FIV B-cell peptides and HIV-1/FIV T-cell peptides used for B-cell and T-cell epitope analyses (see FeIFNγ ELISpot, FIG. 3), respectively, are shown in reference to HIV-1 and FIV sequences. The designations of FIV B-cell peptides and HIV-1/FIV T-cell peptides (peptide code with aa position) are shown on the top right in FIG. 2B. Each bar below the aa alignment represents an overlapping 28-30mer B-cell peptide, which was used in the ELISA analysis for cross-reactive B-cell epitope mapping. The B-cell peptide overlaps by 11-13 aa, except for the four peptides (FB1, FB2, FC2, FB4) on the N-terminal. The 26mer peptide FC2/34-59 is based on $FIV_{FC1}$ sequence and differs from $FIV_{Bang}$ sequence by having $Ser^{48}$ and $Ser^{57}$ instead of $Pro^{48}$ and $Ala^{57}$. HIV-1 and FIV peptide sequences used for T-cell epitopes are shown with red aa. All 18 T-cell peptides (9-11mers) are boxed with dotted line. T-cell peptide code is shown immediately above (HIV-1 p24 peptide) or below (FIV p24 peptide) the dotted box. Overlapping red bars on C-terminal represent two overlapping T-cell epitopes and their corresponding sequences. HIV-1 T-cell peptides are identical to the $HIV\text{-}1_{UCD1}$ peptide sequences. FIV T-cell peptides, except for the four peptide sequences below the alignment (F4/73-83, F4.5/122-131, F5/142-150, F7/183-191), are identical to the $FIV_{Bang}$ peptide sequences. FIV peptides F4/73-83 and F7/183-191 are identical to the corresponding $FIV_{FC1}$ peptide sequences and remaining two FIV peptides, F4.5/122-131 and F5/142-150, are identical to the $FIV_{Shi}$ peptide sequences. The published major homology region (MHR) (Matsuo et al., 1992; Nath et al., 2001) is boxed with a solid line.

FIGS. 3A and 3B show B-cell and T-cell epitope analyses of sera and PBMC from HIV-1 p24-vaccinated cats. Sera from HIV-1 p24-vaccinated/protected cats (n=15) at 3 weeks after 3rd vaccination before challenge and from FIV-infected control cats (n=5) at 18 wpi were tested for reactivity to twelve overlapping B-cell peptides by ELISA (FIG. 3A). These overlapping peptides derived from FIV p24 sequence are shown in FIG. 2 with their peptide designation. The reactivity of the sera is shown as % positive (e.g., number of positive sera among total number of sera tested). The total numbers of sera tested were 15 sera for p24-vaccinated/protected cats (i.e., one vaccinated/protected cat not tested) and 5 select sera for FIV-infected control cats. The B-cell peptide codes (without aa sequence designation) are shown below the corresponding bars. As controls, serum reactivities to $FIV_{Bang}$ and $HIV-1_{UCD1}$ p24 proteins and FIV transmembrane peptide TM(695-705) (Yamamoto et al., 1993) were determined.

Figure 2A:
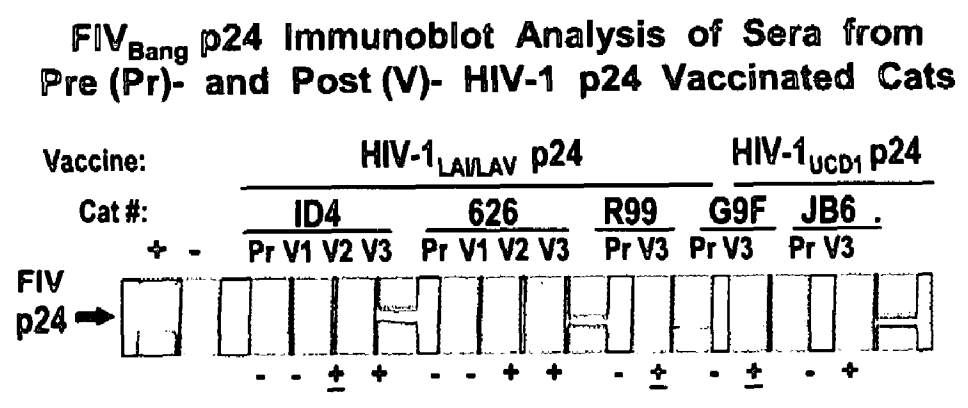
Figure 2B:
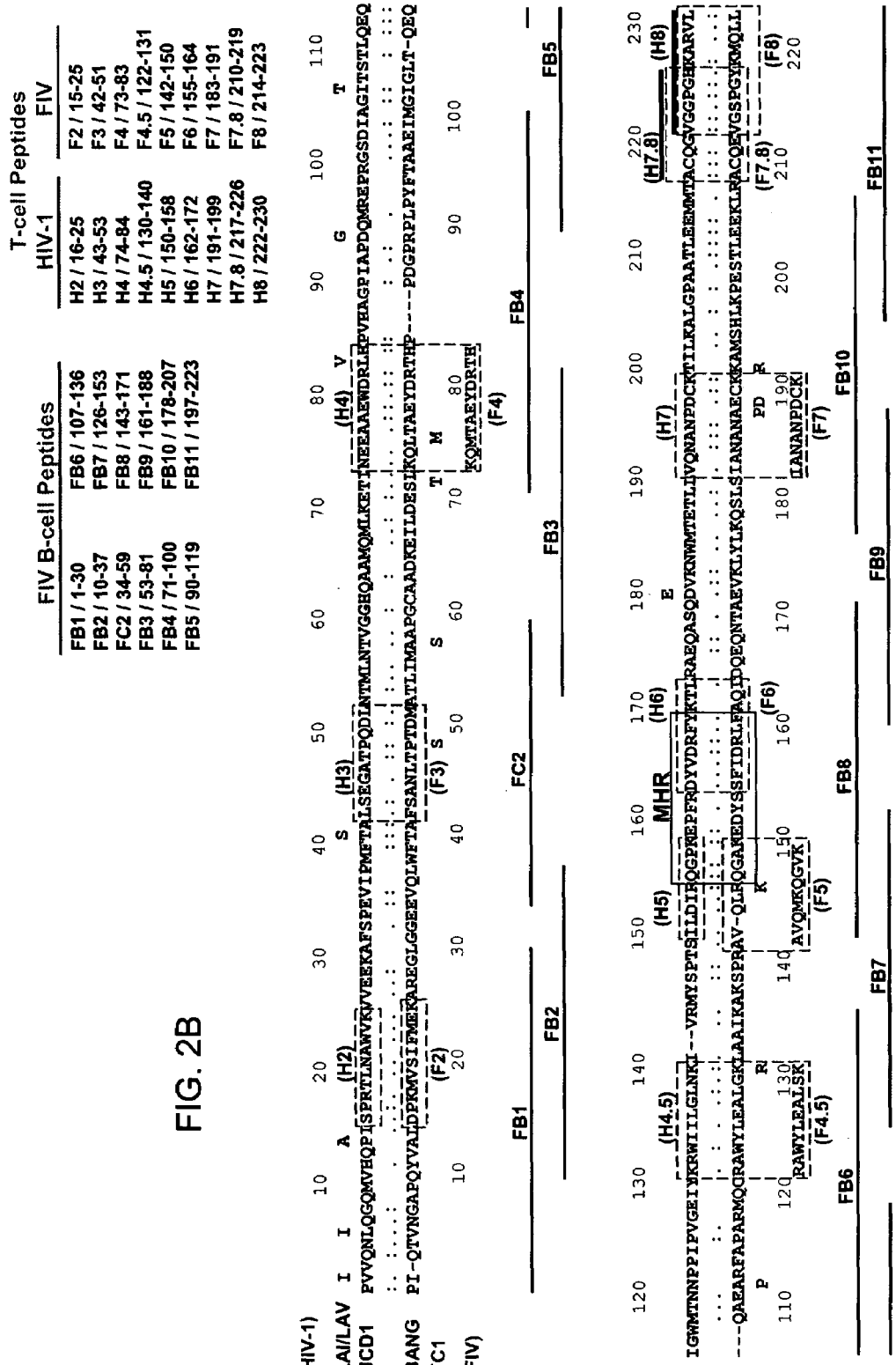
Figure 3A:
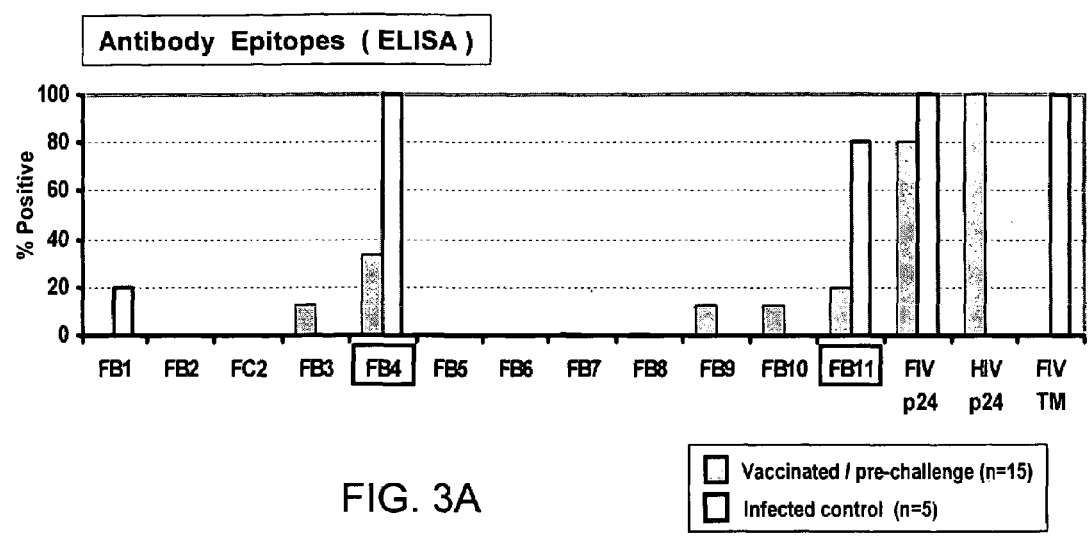
Figure 3B:
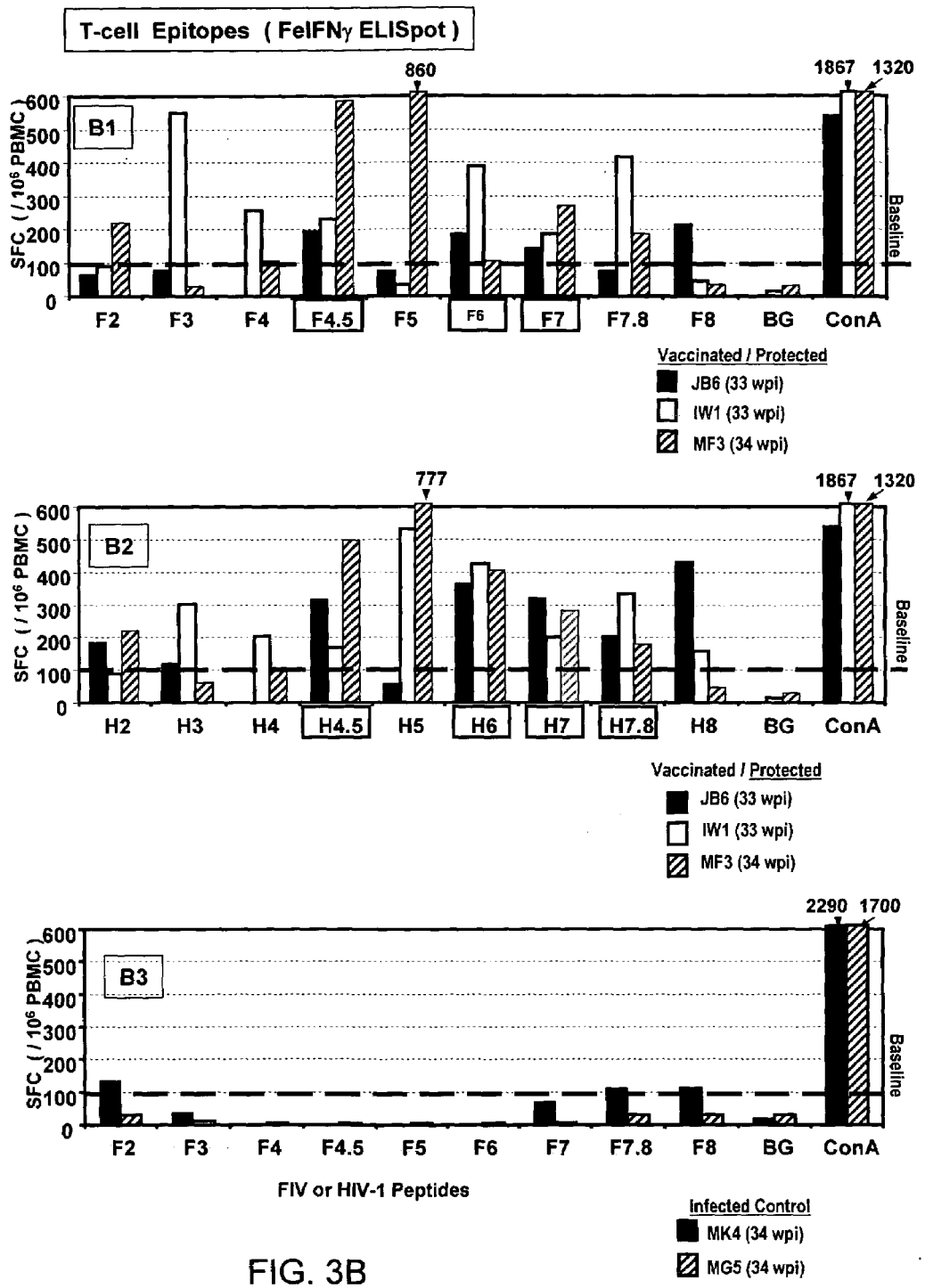

FeIFNγ ELISpot analysis was used to determine the T-cell epitope reactivity of PBMC from vaccinated/protected cats and infected control cats (panels B1, B2, B3 of FIG. 3B). The PBMC from three vaccinated/protected cats (#JB6 and #IW1, Study 3; #MF3, Study 4) (panels B1, B2) and two FIV-infected control cats (#MK4 and #MG5, Study 4) (panel B3) at 33-34 wpi were evaluated for FeIFNγ ELISpot responses to nine FIV p24 peptides (described in FIG. 2) (panels B1, B3), nine corresponding HIV-1 p24 peptides (described in FIG. 2) (panel B2), non-specific scrambled peptide, concanavalin A (ConA, 0.2 μg/0.2 μl/well) (positive control), and no peptides (media background, BG). The results are shown as mean spot forming cells (SFC) per $10^6$ PBMC of duplicate-triplicate samples with standard deviation (SD) of 3-15% (SD not shown). Individual bar above each T-cell peptide code represents a result from one cat and the bar designations of each cat are shown in the panels. The PBMC from all cats had no significant response to scrambled peptide (<20 SPC/$10^6$ PBMC) (data not shown).

BRIEF DESCRIPTION OF THE SEQUENCES

SEQ ID. NO: 1 is an amino acid sequence of an $HIV-1_{UCD1}$ envelope protein.

SEQ ID NO: 2 is an amino acid sequence of an $HIV-1_{UCD1}$ gag protein.

SEQ ID NO: 3 is a nucleotide sequence of an $HIV-1_{UCD1}$ polynucleotide encoding an envelope protein.

SEQ ID NO: 4 is a nucleotide sequence of an $HIV-1_{UCD1}$ polynucleotide encoding a gag protein.

SEQ ID. NO: 5 is an amino acid sequence of an $HIV-1_{IIIB}$ envelope protein.

SEQ ID NO: 6 is an amino acid sequence of an $HIV-1_{IIIB}$ gag protein.

SEQ ID NO: 7 is a nucleotide sequence of an $HIV-1_{IIIB}$ polynucleotide encoding an envelope protein.

SEQ ID NO: 8 is a nucleotide sequence of an $HIV-1_{IIIB}$ polynucleotide encoding a gag protein.

SEQ ID NO: 9 is an amino acid sequence of a peptide fragment (H2) of an HIV protein that can be used according to the subject invention.

SEQ ID NO: 10 is an amino acid sequence of a peptide fragment (H3) of an HIV protein that can be used according to the subject invention.

SEQ ID NO: 11 is an amino acid sequence of a peptide fragment (H4) of an HIV protein that can be used according to the subject invention.

SEQ ID NO: 12 is an amino acid sequence of a peptide fragment (H4.5) of an HIV protein that can be used according to the subject invention.

SEQ ID NO: 13 is an amino acid sequence of a peptide fragment (H5) of an HIV protein that can be used according to the subject invention.

SEQ ID NO: 14 is an amino acid sequence of a peptide fragment (H6) of an HIV protein that can be used according to the subject invention.

SEQ ID NO: 15 is an amino acid sequence of a peptide fragment (H7) of an HIV protein that can be used according to the subject invention.

SEQ ID NO: 16 is an amino acid sequence of a peptide fragment (H7.8) of an HIV protein that can be used according to the subject invention.

SEQ ID NO: 17 is an amino acid sequence of a peptide fragment (H8) of an HIV protein that can be used according to the subject invention.

SEQ ID NO: 18 is an amino acid sequence of a peptide fragment (F2) of an FIV protein that can be used according to the subject invention.

SEQ ID NO: 19 is an amino acid sequence of a peptide fragment (F3) of an FIV protein that can be used according to the subject invention.

SEQ ID NO: 20 is an amino acid sequence of a peptide fragment (F4) of an FIV protein that can be used according to the subject invention.

SEQ ID NO: 21 is an amino acid sequence of a peptide fragment (F4.5) of an FIV protein that can be used according to the subject invention.

SEQ ID NO: 22 is an amino acid sequence of a peptide fragment (F5) of an FIV protein that can be used according to the subject invention.

SEQ ID NO: 23 is an amino acid sequence of a peptide fragment (F6) of an FIV protein that can be used according to the subject invention.

SEQ ID NO: 24 is an amino acid sequence of a peptide fragment (F7) of an FIV protein that can be used according to the subject invention.

SEQ ID NO: 25 is an amino acid sequence of a peptide fragment (F7.8) of an FIV protein that can be used according to the subject invention.

SEQ ID NO: 26 is an amino acid sequence of a peptide fragment (F8) of an FIV protein that can be used according to the subject invention.

SEQ ID NO: 27 is an amino acid sequence of a peptide fragment (FB1) of an FIV protein that can be used according to the subject invention.

SEQ ID NO: 28 is an amino acid sequence of a peptide fragment (FB2) of an FIV protein that can be used according to the subject invention.

SEQ ID NO: 29 is an amino acid sequence of a peptide fragment (FC2) of an FIV protein that can be used according to the subject invention.

SEQ ID NO: 30 is an amino acid sequence of a peptide fragment (FB3) of an FIV protein that can be used according to the subject invention.

SEQ ID NO: 31 is an amino acid sequence of a peptide fragment (FB4) of an FIV protein that can be used according to the subject invention.

SEQ ID NO: 32 is an amino acid sequence of a peptide fragment (FB5) of an FIV protein that can be used according to the subject invention.

SEQ ID NO: 33 is an amino acid sequence of a peptide fragment (FB6) of an FIV protein that can be used according to the subject invention.

SEQ ID NO: 34 is an amino acid sequence of a peptide fragment (FB7) of an FIV protein that can be used according to the subject invention.

SEQ ID NO: 35 is an amino acid sequence of a peptide fragment (FB8) of an FIV protein that can be used according to the subject invention.

SEQ ID NO: 36 is an amino acid sequence of a peptide fragment (FB9) of an FIV protein that can be used according to the subject invention.

SEQ ID NO: 37 is an amino acid sequence of a peptide fragment (FB10) of an FIV protein that can be used according to the subject invention.

SEQ ID NO: 38 is an amino acid sequence of a peptide fragment (FB11) of an FIV protein that can be used according to the subject invention.

SEQ ID NO: 39 is an amino acid sequence of a peptide fragment (HIV MHR) of an HIV protein that can be used according to the subject invention.

SEQ ID NO: 40 is an amino acid sequence of a peptide fragment (FIV MHR) of an FIV protein that can be used according to the subject invention.

SEQ ID NO: 41 is an amino acid sequence of a peptide fragment (F3.I) of an FIV protein that can be used according to the subject invention.

SEQ ID NO: 42 is an amino acid sequence of a peptide fragment (F4.5.I) of an FIV protein that can be used according to the subject invention.

SEQ ID NO: 43 is an amino acid sequence of a peptide fragment (F4.5.B) of an FIV protein that can be used according to the subject invention.

SEQ ID NO: 44 is an amino acid sequence of a peptide fragment (F5.B) of an FIV protein that can be used according to the subject invention.

SEQ ID NO: 45 is an amino acid sequence of a peptide fragment (F5.I) of an FIV protein that can be used according to the subject invention.

SEQ ID NO: 46 is an amino acid sequence of a peptide fragment (F7.B) of an FIV protein that can be used according to the subject invention.

Detailed Disclosure of the Invention

The subject invention concerns materials and methods for protecting a feline animal from infection by FIV by administering to the animal immunogens derived from primate immunodeficiency viruses, such as human immunodeficiency virus (HIV) or simian immunodeficiency virus (SIV). In one embodiment, an effective amount of a composition comprising an immunogen or immunogens derived from a primate immunodeficiency virus is administered to a feline animal. In addition, the various immunogen compositions described herein can be used separately and in combination with each other.

Advantageously, the present invention allows for protection against FIV infection wherein the generation of an immune response against FIV in the animal allows a veterinarian or other person of ordinary skill in the art to determine whether an animal's immune response to FIV or FIV immunogens or antigens is a result of an immunization to protect against FIV infection or if it is a result of FIV infection in the animal. In one embodiment, animals immunized using a composition of the present invention do not produce antibodies that cross-react with FIV gp95. Animals that have been infected with FIV or that may have received vaccines containing FIV-derived immunogens or antigens produce antibodies that bind to FIV gp95. Feline animals encompassed within the scope of the present invention include domestic house cats, feral cats, and other wild cats including bobcat, cougar, mountain lion, tiger, jaguar, leopard, puma, cheetah, and lion.

The present invention can also be used to generate an immune response, cellular and/or humoral, against FIV in a feline animal using immunogens derived from primate immunodeficiency viruses, such as HIV and SIV. In one embodiment, an amount of an immunogen sufficient to induce an immune response against FIV is administered to a feline animal. Serum antibodies from immunized cats can be tested for virus neutralizing antibody activity against HIV using PBMCs from healthy HIV-uninfected humans as indicator cells. Lymphocytes from immunized cats can be tested for both HIV-specific T-helper (Th) and cytotoxic T lymphocyte (CTL) activities. Th and CTL activity can be measured by the level of Th cytokines and CTL cytotoxins produced by the lymphocytes from unimmunized and immunized cats in response to in vitro stimulation with inactivated HIV wholevirus that are either the same as (homologous) or different from (heterologous to) the immunogen strain(s). The inactivated heterologous strains used for the in vitro stimulation can be from the same or different subtypes as the immunogen strain(s). Preferred immunogens produce high levels of Th cytokines in the cultures with $CD4^+$ T lymphocytes from immunized cats and/or induce strong Th activity against FIV and/or HIV. Similarly, preferred immunogens produce high levels of CTL cytotoxin(s) by $CD8^+$ T lymphocytes from immunized cats and/or induce strong CTL activity against FIV and/or HIV.

Primate immunodeficiency viruses encompassed within the scope of the methods and materials of the present invention include HIV and SIV. In regard to HIV, the virus can be from either HIV-1 or HIV-2. In one embodiment, the HIV is HIV-1. Several distinct strains of HIV-1 have been described in the art and include, for example, $HIV-1_{IIIB}$, $HIV-1_{UCD1}$, $HIV-1_{LAI/LAV}$, and $HIV-1_{BRU}$. In an exemplified embodiment described herein, immunogens of the present invention are derived from the strain of HIV-1 designated as $HIV-1_{IIIB}$ and/or $HIV-1_{UCD1}$. SIV strains within the scope of the invention include, but are not limited to, $SIV_{syk}$, $SIV_{smm}$, $SIV_{mac}$, $SIV_{mnd}$, $SIV_{l'hoest}$, $SIV_{agm}$ and $SIV_{cpz}$ (Whetter et al., 1999). The nucleotide sequences of numerous HIV and SIV genes have been described in the scientific literature, deposited in sequence databanks, such as the NCBI Genbank, and have been disclosed in published patent applications and issued patents. For example, complete genome sequences of HIV-1 and HIV-2 isolates are disclosed at Genbank accession numbers NC 001802 and NC 001722 and complete genome sequences of SIV are disclosed at Genbank accession numbers L06042, AF131870, M32741, and M66437. Similarly, amino acid sequences of proteins encoded by HIV and SIV genes have been disclosed and are well known in the art. Sequences of HIV are also disclosed in databases available at the website http://www.hiv.lanl.gov/content/index. Genes of primate immunodeficiency viruses that encode proteins that can be used in the present invention, but are not limited to, include env, gag, pol, and nef and fragments and subunits thereof.

Immunogens derived from primate immunodeficiency viruses can be in isolated form or provided in any suitable composition. Preferably, the primate immunodeficiency viral immunogens are provided in a composition and administered in a manner to induce a strong cell-mediated and humoral immune response to the immunogen in a feline animal. In one embodiment, immunogens can be provided in the form of virus infected cells or whole cell-free virus. Virus in virus-infected cells and cell-free virus can be treated in a manner to inactivate or attenuate the virus. Methods for inactivating or attenuating virus are known in the art, and include, for example, treatment with paraformaldehyde, formalin, phenol, UV light, elevated temperature and the like. U.S. Pat. No. 6,503,753 describes methods for photoinactivation of HIV reverse transcriptase which thereby inactivates the HIV virus.

Primate immunodeficiency viruses can also be prepared that are replication-defective. U.S. Pat. No. 6,500,623 describes HIV replication-defective viral particles and means for producing them. Other techniques for producing inactivated, attenuated and replication defective viruses are known in the art.

In another embodiment, immunogens of the invention are derived from viral proteins, or immunogenic fragments or variants thereof, of primate immunodeficiency viruses. Proteins that can be utilized as immunogens in the present invention include, but are not limited to, proteins encoded by the env, gag, pol, tat, rev, and/or nef genes. In one embodiment, envelope proteins encoded by the env gene that can be used in the invention include the envelope proteins gp120 and gp160, including fragments thereof, fusions of gp120 and gp160, and variations of gp120 and gp160, including variations in glycosylation which includes gp120 and/or gp160 proteins that are unglycosylated. A cellular protein cleaves gp160 into gp41 and gp120 moieties. The gp41 moiety comprises the transmembrane domain of the envelope protein, whereas gp120 is located on the surface of the infected cell or virion. The gp120 molecule consists of a polypeptide core of approximately 60 kd, but N-linked glycosylation can increase the molecular weight of the protein to approximately 120 kd. The viral envelope proteins used in conjunction with the present invention can be either unclipped or clipped (see, for example, U.S. Pat. No. 5,849,533). Envelope protein variants have been described in U.S. Pat. No. 5,846,546. Synthetic peptides which immunologically mimic HIV gp120 and/or gp160 envelope proteins can also be used in the present invention (see, for example, U.S. Pat. No. 5,763,160). In an exemplified embodiment, a combination of gp120 and gp160 envelope protein from HIV-$1_{IIIB}$ is utilized as an immunogen. In one embodiment, the envelope polypeptide of HIV-$1_{UCD\text{-}1}$ comprises the amino acid sequence shown in SEQ ID NO: 1. In one embodiment, the envelope polypeptide of HIV-$1_{IIIB}$ comprises the amino acid sequence shown in SEQ ID NO: 5.

Proteins encoded by a primate immunodeficiency virus gag gene, such as the p17 matrix protein, the p24 capsid protein, and the p7 nucleocapsid protein of HIV and the p27 protein of SIV, and fragments and variants thereof, can also be used in accordance with the present invention. In an exemplified embodiment, a p24 protein from HIV-$1_{UCD\text{-}1}$ is utilized as an immunogen. In one embodiment, the p24 polypeptide of HIV-$1_{UCD\text{-}1}$ comprises amino acids 132 to 362 of SEQ ID NO: 2. In one embodiment, the p24 polypeptide of HIV-$1_{IIIB}$ comprises amino acids 132 to 363 of SEQ ID NO: 6. Immunological fragments of the p24 protein have been described in U.S. Pat. No. 5,700,469.

Proteins encoded by a primate immunodeficiency virus pol gene, such as reverse transcriptase (RT), protease (PR), and Rnase H of HIV, and fragments and variants thereof, can also be used in the present invention. Endonuclease protein p31 of HIV, and fragments and variants thereof, which is a protein encoded at the 3'-end of the pol gene of HIV, can also be used in accordance with the present invention. Immunological peptide fragments of the p31 protein of HIV have been described in U.S. Pat. No. 5,401,628. Regulatory proteins encoded by tat and rev genes of primate immunodeficiency viruses, and accessory proteins encoded by nef, vif, vpr, vpu, and vpx genes of primate immunodeficiency viruses, and fragments and variants of these proteins, can also be used in the present invention.

Peptides corresponding to immunogenic or antigenic regions of primate immunodeficiency viruses can be synthesized or prepared by recombinant means and utilized in the methods of the present invention. In one embodiment, peptides that correspond to overlapping fragments of a primate immunodeficiency virus protein can be prepared and used in the methods of the present invention. Any suitable combination of the peptide fragments can be used for immunizing an animal according to methods of the present invention. For example, peptide fragments that correspond to the carboxy terminus region of a viral protein can be used with peptide fragments that correspond to an amino terminus region or a transmembrane region of the protein.

Recombinant virus or viral vector-based expression constructs that comprise, primate immunodeficiency virus nucleotide sequences, for example, HIV or SIV env, gag, pol, tat, rev, nef, vif, vpu, vpr, gag/pol, or env-gag/pol sequences, or fragments or variants thereof, are also contemplated for use with the present invention. Any suitable viral vector that can be used to prepare recombinant vector/HIV or recombinant vector/SIV constructs is contemplated for use with the subject invention. For example, viral vectors derived from adenovirus, avipox, feline herpesvirus, vaccinia, canarypox, entomopox, swinepox and others known in the art can be used with the compositions and methods of the present invention. Recombinant polynucleotide vectors that encode and that can express HIV or SIV components in a suitable host cell can be constructed using standard genetic engineering techniques known in the art.

DNA or RNA vaccines which comprise nucleic acid that encodes one or more primate immunodeficiency virus proteins, or a fragment or variant thereof, are also contemplated for use in the subject invention. The nucleic acid can be provided in the form of a plasmid or eukaryotic expression construct. DNA vaccines and formulations have been described, for example, in published patent applications 20040076632; 20040047878; 20040009941; 20020156037; 20020032165; and 20010004531.

As used herein, the term “expression construct” refers to a combination of nucleic acid sequences that provides for transcription of an operably linked nucleic acid sequence. As used herein, the term “operably linked” refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the immunogens of the invention. Chemical enhancers are cis-acting elements that increase gene transcription and can also be included in the expression construct. Chemical enhancer elements are known in the art, and include, but are not limited to, the cytomegalovirus (CMV) early promoter enhancer element and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPO-FECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced as naked DNA using methods known in the art, such as transfection, microinjection, electroporation, calcium phosphate precipitation, and by biolistic methods.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the exemplified sequences. The polynucleotide includes both the sense and antisense strands as either individual strands or in the duplex.

The methods of the present invention contemplate a primary immunization with a vaccine composition of the invention. Subsequent or secondary immunizations are also contemplated within the scope of the subject methods. The vaccine composition used for secondary immunizations can be the same as or vary from the composition used for primary immunization. For example, primary immunizations of an animal may use recombinant vector-based HIV or SIV constructs, having single or multiple strain components, followed by secondary boosts with vaccine compositions comprising HIV- or SIV-infected cell lines, or HIV or SIV polypeptides, or cell free HIV or SIV virus, also having single or multiple strain components. Primary immunizations can also use an HIV and/or SIV DNA vaccine. In one embodiment, a recombinant vector construct is used for the primary immunization, whereas a protein, or protein plus recombinant vector construct, subunit vaccine composition is used for secondary boosts. In addition, the subject invention contemplates methods wherein the immunogen(s) used for a primary immunization is an HIV or SIV derived immunogen, e.g., an HIV p24 protein, and the immunogen(s) used for secondary immunizations are derived from FIV, e.g., FIV gp95 and/or gp36 protein, or whole FIV virus, or FIV-infected cells. Other immunization protocols with the vaccine compositions of the invention are apparent to persons skilled in the art and are contemplated within the scope of the present invention.

In one embodiment, immunogens from various primate immunodeficiency viral proteins are combined for administration to an animal. For example, immunogens from any of HIV p7, p17, p24, gp41, gp120, and gp160 can be combined for administration. In an exemplified embodiment, a composition comprising an immunogen of HIV-1 p24 and an immunogen of HIV-1 gp120 and gp160 is administered to a feline animal. In another exemplified embodiment, a composition comprising HIV-1 p24 as the only immunogen is administered to a feline animal.

The subject invention also concerns materials and methods for protecting a feline animal against infection by an FIV or for generating an immune response against an FIV by administering to the animal a composition comprising immunogens derived from primate immunodeficiency viruses and immunogens derived from FIV. FIV-derived immunogens have been described in the art. See, for example, U.S. Pat. Nos. 5,118,602; 5,565,319; 5,510,106; 5,275,813; 5,037,753; and 4,861,720. FIV immunogens that can be used in accordance with the subject invention can be either of a single subtype or strain of FIV, or the immunogen can be derived from multiple subtypes of FIV. Multi-subtype FIV immunogens have been described in U.S. Pat. Nos. 5,846,825; 6,254,872; and 6,447,993.

In one embodiment of the subject methods, the immunogen to be administered to a feline animal comprises an epitope that is conserved between the primate immunodeficiency virus and FIV. In a further embodiment, the conserved epitope is present in the envelope protein of an immunodeficiency virus. Also contemplated within the scope of the invention are molecules (mimotope) which have a conformation that has a topology equivalent to a conserved epitope of the present invention and which binds to the same antigen-binding region of an antibody that binds to the conserved epitope. Typically, mimotopes are peptide molecules, but mimotopes can also be prepared from other non-peptide molecules.

The subject invention also concerns immunogens derived from a primate immunodeficiency virus, wherein the immunogen is a protein or peptide and comprises an epitope conserved between the primate immunodeficiency virus and FIV. In an exemplified embodiment, the immunogen comprises a gp120 and gp160 protein from HIV-1$_{IIIB}$ or an immunogenic fragment or variant thereof, and, optionally, a p24 protein from HIV$_{UCD1}$, or an immunogenic fragment or variant thereof. In another embodiment, the immunogen comprises a p24 protein from HIV$_{UCD1}$, or an immunogenic fragment or variant thereof. The subject invention also concerns polynucleotides that encode the protein or peptides comprising conserved epitopes of the immunodeficiency virus derived immunogens.

The subject invention also concerns antibodies that cross-react with epitopes of the immunogens derived from primate immunodeficiency viruses and FIV. The antibodies can be polyclonal or monoclonal in form. The antibodies can be derived from any animal capable of producing antibodies to the epitopes, and include, for example, human, ape, monkey, mouse, rat, goat, sheep, pig, cow, and feline animals. Also contemplated within the scope of the invention are non-human antibodies that cross-react with an epitope of the immunogen derived from a primate immunodeficiency virus and FIV but that have been "humanized" using standard procedures known in the art, such as those described in U.S. Pat. Nos. 5,530,101; 5,585,089; 5,693,762; 6,180,370; and 6,407,213.

Peptide and/or polypeptide immunogens of the present invention can also be provided in the form of a multiple antigenic peptide (MAP) construct. The preparation of MAP constructs has been described in Tam (1988). MAP constructs utilize a core matrix of lysine residues onto which multiple copies of an immunogen are synthesized (Posnett et al., 1988). Multiple MAP constructs, each containing the same or different immunogens, can be prepared and administered in a vaccine composition in accordance with methods of the present invention. In one embodiment, a MAP construct is provided with and/or administered with one or more adjuvants.

Natural, recombinant or synthetic polypeptides of primate immunodeficiency viral proteins, and peptide fragments thereof, can also be used as vaccine compositions according to the subject methods. In one embodiment, different polypeptides are administered as a combined preparation to a feline animal. In an exemplified embodiment, HIV-1 gp120/160 and HIV-1 p24 polypeptides are administered to a feline animal. In another embodiment, HIV polypeptides derived from more than one HIV strain are combined in a vaccine composition and are used to vaccinate a host animal. For example, polypeptides based on the HIV envelope glycoprotein from at least two strains of HIV-1 can be combined in the vaccine. The polypeptides may comprise "hybrid" or "chimeric" polypeptides whose amino acid sequence is derived from joining or linking polypeptides from at least two distinct HIV strains. Procedures for preparing HIV polypeptides are well known in the art. For example, HIV polypeptides can be synthesized using solid-phase synthesis methods (Merrifield, 1963). HIV polypeptides can also be produced using recombinant DNA techniques wherein a polynucleotide molecule encoding an HIV protein or peptide is expressed in a host cell, such as bacteria, yeast, or mammalian cell lines, and the expressed protein purified using standard techniques of the art.

According to the methods of the subject invention, the immunogenic compositions described herein are administered to susceptible hosts, typically domestic cats, in an effective amount and manner to induce protective immunity against subsequent challenge or infection of the host by FIV. The immunogens are typically administered parenterally, by injection, for example, either subcutaneously, intraperitoneally, or intramuscularly, or by oral or nasal administration, or any combination of such routes of administration. Usually, the immunogens are administered to a host animal at least two times, with an interval of one or more weeks between each administration. However, other regimens for the initial and booster administrations of the immunogens are contemplated, and may depend on the judgment of the practitioner and the particular host animal being treated.

Immunogens that can be used in accordance with the present invention can be provided with a pharmaceutically-acceptable carrier or diluent. Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin, Easton Pa., Mack Publishing Company, $19^{th}$ ed., 1995, describes formulations which can be used in connection with the subject invention. In general, the compositions of the subject invention will be formulated such that an effective amount of an immunogen is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of an immunogen of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the immunogen or immunogens based on the weight of the total composition including carrier or diluent.

The immunogenic compositions of the subject invention can be prepared by procedures well known in the art. For example, the immunogens are typically prepared as injectables, e.g., liquid solutions or suspensions. The immunogens are administered in a manner that is compatible with dosage formulation, and in such amount as will be therapeutically effective and immunogenic in the recipient. The optimal dosages and administration patterns for a particular immunogens formulation can be readily determined by a person skilled in the art.

As noted above, virus and cells in a immunogenic formulation may be inactivated or attenuated using methods known in the art. The amount of cell-free whole or partial virus in a vaccine dose will usually be in the range from about 0.1 mg to about 5 mg, and more usually being from about 0.2 mg to about 2 mg. The dosage for formulations comprising virus-infected cell lines will usually contain from about $10^6$ to about $10^8$ cells per dose, and more usually from about $5 \times 10^6$ to about $7.5 \times 10^7$ cells per dose. The amount of protein or peptide immunogen in a dose for a feline animal can vary from about 0.1 µg to 10000 µg, or about 1 µg to 5000 µg, or about 10 µg to 1000 µg, or about 25 µg to 750 µg, or about 50 µg to 500 µg, or 100 µg to 250 µg, depending upon the size, age, etc., of the animal receiving the dose.

In one embodiment, an immunogen of the invention is provided with one or more adjuvants that increase the animal's immune response against the immunogen. Immunogens of the invention can be provided with and/or administered with any suitable adjuvant or adjuvants known in the art. In one embodiment, the adjuvant is one that helps induce a strong cellular immune response. Adjuvants that can be used in the immunogen formulations of the invention include threonyl muramyl dipeptide (MDP) (Byars et al., 1987), Ribi adjuvant system components (Corixa Corp., Seattle, Wash.) including the cell wall skeleton (CWS) component, Freund's complete, and Freund's incomplete adjuvants, bacterial lipopolysaccharide (LPS), such as from *E. coli*, or a combination thereof. A variety of other adjuvants suitable for use with the methods and vaccines of the subject invention, such as alum, aluminum hydroxide, and saponin are well known in the art and are contemplated for use with the subject invention. Cytokines (γ-IFN, GM-CSF, CSF, etc.) and lymphokines and interleukins (IL-1, IL-2, IL-3, IL-4, IL-5, IL-6, IL-7, IL-8. IL-9, IL-10, IL-11, IL-12, IL-13, IL-14, IL-15, IL-16, IL-17, IL-18, IL-19, IL-20, IL-21, and IL-22) have also been used as adjuvants and/or supplements to vaccine compositions and are contemplated within the scope of the present invention. One or more different cytokines and lymphokines can be included in a composition comprising an immunogen of the invention. In one embodiment, an immunogen of the invention is administered to an animal in combination with the lymphokine interleukin-12 (IL-12) in combination with another adjuvant. Also specifically contemplated within the scope of the invention is the use of the lymphokine interleukin-18 (IL-18) as part of an adjuvant composition. In one embodiment, an adjuvant composition used with the subject invention comprises a combination of IL-12 and IL-15, or IL-15 and IL-18, or IL-12 and IL-18, or IL-12, IL-15, and IL-18. The cytokine selected is of a species that has biological activity in the animal receiving the immunogen. For example, if the animal is a cat, then the cytokine can be a human cytokine or a feline cytokine, e.g., feline IL-12, feline IL-15, feline IL-18, etc. In an exemplified embodiment, a primate derived immunogen, such as HIV-1 p24, is administered in combination with Ribi adjuvant system component including CWS and IL-12 and/or IL-18.

Abbreviations of FIV strains used herein are shown below:

| Strain (subtype) | Abbreviation |
| --- | --- |
| Petaluma (A) | $FIV_{Pet}$ |
| Dixon (A) | $FIV_{Dix}$ |
| UK8 (A) | $FIV_{UK8}$ |
| Bangston (B) | $FIV_{Bang}$ |
| Aomori-1 (B) | $FIV_{Aom1}$ |

-continued

| Strain (subtype) | Abbreviation |
| --- | --- |
| Aomori-2 (B) | $FIV_{Aom2}$ |
| FC1 (B) | $FIV_{FC1}$ |
| Shizuoka (D) | $FIV_{Shi}$ |
| Dutch113 (A) | $FIV_{Dut113}$ |
| Dutch19K (A) | $FIV_{Dut19}$ |
| UK2 (A) | $FIV_{UK2}$ |
| SwissZ2 (A) | $FIV_{SwiZ2}$ |
| Sendai-1 (A) | $FIV_{Sen1}$ |
| Sendai-2 (B) | $FIV_{Sen2}$ |
| USCAzepy01A (A) | FIV |
| USCAhnky11A (A) | $FIV_{USC11}$ |
| USCAtt-10A (A) | $FIV_{USC10}$ |
| USCAlemy01 (A) | FIV |
| USCAsam-01A (A) | FIV |
| PPR (A) | $FIV_{PPR}$ |
| FranceWo | $FIV_{Fra}$ |
| Netherlands | $FIV_{Net}$ |
| USILbrny03B (B) | $FIV_{USI03}$ |
| TM2 (B) | $FIV_{TM2}$ |
| USCKlgri02B (B) | $FIV_{USC02}$ |
| Yokohama (B) | $FIV_{Yok}$ |
| USMAsboy03B (B) | $FIV_{USMA03}$ |
| USTXmtex03B (B) | $FIV_{UST03}$ |
| USMCglwd03B (B) | $FIV_{USMC03}$ |
| CABCpbar03C (C) | $FIV_{CAB03}$ |
| CABCpbar07C (C) | $FIV_{CAB07}$ |
| CABCpady02C (C) | $FIV_{CAB02}$ |
| Fukuoka (D) | $FIV_{Fuku}$ |

The subject invention also concerns methods of use of an animal model for selecting for epitopes conserved between immunodeficiency viruses, such as HIV and FIV, that can be used to immunize a person or animal against infection by an immunodeficiency virus. In one embodiment of the method, HIV is isolated from an HIV-infected, long-term nonprogressor patient. As used herein, the term "long-term nonprogressors" refers to HIV-infected patients that exhibit a stable CD4 count for at least 10 years, exhibit a low virus load (i.e., virus level in plasma is low to undetectable as measured by RT-PCR) and typically exhibit few or no disease symptoms. Immunogens from the isolated HIV are prepared and used to immunize a feline animal, such as a domestic cat. In one embodiment of the method, peptide fragments of an HIV protein are used as immunogens. Preferably, overlapping fragments that represent the full length of the HIV protein are prepared for use as immunogens. In one embodiment, different combinations of the peptide fragments are administered to different cats in order to identify those fragments that contain epitopes that provide the strongest prophylactic protection against FIV infection. Immunized cats are subsequently challenged with FIV. Immunogens that protect a cat against infection when challenged with FIV comprise evolutionarily conserved epitopes and can be used as immunogens to immunize humans, feline animals, and other mammals against infection by immunodeficiency viruses. Preferably, the immunogen protects a cat against infection by FIV of more than one subtype. Fragments of an immunogen comprising an evolutionarily conserved epitope can be prepared and tested using the subject method to further isolate the epitope. Fragments can also be sequenced to determine the primary amino acid sequence of the epitope. In a preferred embodiment, an immunogen comprising an evolutionarily conserved epitope selected using the subject method can be used to immunize a human against infection from HIV. In one embodiment of the method, the immunogen used to immunize cats is an HIV p24 protein, or an immunogenic fragment thereof. The subject invention also concerns evolutionarily conserved epitopes of immunodeficiency viruses identified using the subject method.

The subject invention also concerns methods for inducing an immune response in humans and other animals, such as cats and other felids, against immunogens, antigens, or viruses comprising epitopes that are evolutionarily conserved among immunodeficiency viruses, such as HIV and FIV. In one embodiment, an immunogen(s) or antigen(s) comprising one or more evolutionarily conserved epitope(s) from an immunodeficiency virus(es) identified by methods described herein is administered to a person or animal in an amount and for a duration sufficient to induce an immune response against the immunogen or antigen and any virus or cell displaying or having the immunogen or antigen. The immune response induced can be humoral or cell-mediated or both. In one embodiment for inducing an immune response against HIV, a human is administered an effective amount of an immunogen comprising an evolutionarily conserved epitope identified from an HIV. Immunogens contemplated within the scope of the invention include, but are not limited to, an HIV p24 protein, or an immunogenic fragment thereof. In one embodiment, an immunogen used in the present method comprises an HIV-1$_{UCD1}$ p24 protein, or an immunogenic fragment thereof. In a specific embodiment, at least one immunogen is an HIV peptide of the invention comprising an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In a further embodiment for inducing an immune response against HIV, a human is administered an immunogen comprising an evolutionarily conserved epitope identified from an FIV. In one embodiment, an immunogen used in the present method comprises an FIV p24 protein, or an immunogenic fragment thereof. In a specific embodiment, at least one immunogen is an FIV peptide of the invention comprising an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46.

In one embodiment for inducing an immune response in a feline animal against FIV, the animal is administered an immunogen comprising an evolutionarily conserved epitope identified from an HIV. In one embodiment, an immunogen used in the present method comprises an HIV-1 p24 protein, or an immunogenic fragment thereof. In a specific embodiment, at least one immunogen is an HIV peptide of the invention comprising an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In a further embodiment for inducing an immune response in a feline animal against FIV, the animal is administered an immunogen comprising an evolutionarily conserved epitope identified from an FIV. In one embodiment, an immunogen used in the present method comprises an FIV p24 protein, or an immunogenic fragment thereof. In a specific embodiment, at least one immunogen is an FIV peptide of the invention comprising an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46.

The subject invention also concerns methods for treating and protecting humans, and other animals, such as cats and other felids, against infection by immunodeficiency viruses, such as HIV and FIV. In one embodiment of the method, an effective amount of an immunogen(s) or antigen(s) comprising one or more evolutionarily conserved epitope(s) from an immunodeficiency virus(es) identified by methods described herein is administered to a person or animal for a duration sufficient to immunize a person or animal and provide the person or animal with some level of protection against infection by an immunodeficiency virus. In one embodiment for treatment or protection against HIV infection, a human is immunized with an immunogen comprising an evolutionarily conserved epitope identified from an HIV. Immunogens contemplated within the scope of the invention include, but are not limited to, an HIV p24 protein, or an immunogenic fragment thereof. In one embodiment, an immunogen used in the present method comprises an HIV-1$_{UCD1}$, HIV-1$_{LAI/LAV}$, or HIV-1$_{IIIB}$ p24 protein, or an immunogenic fragment thereof. In a specific embodiment, at least one immunogen is an HIV peptide of the invention comprising an amino acid sequence shown in any of SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In another embodiment for treatment or protection against HIV infection, a person is immunized with an immunogen comprising an evolutionarily conserved epitope identified from an FIV. In one embodiment, an immunogen used in the present method comprises an FIV p24 protein, or an immunogenic fragment thereof. In a specific embodiment, at least one immunogen is an FIV peptide of the invention comprising an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46.

In one embodiment for treating or protecting a feline animal from infection by FIV, the animal is administered an immunogen comprising an evolutionarily conserved epitope identified from an HIV. In one embodiment, an immunogen used in the present method comprises an HIV-1 p24 protein, or an immunogenic fragment thereof. In a specific embodiment, at least one immunogen is an HIV peptide of the invention comprising an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In a further embodiment for protecting a feline animal from infection by FIV, the animal is administered an immunogen comprising an evolutionarily conserved epitope identified from an FIV. In one embodiment, an immunogen used in the present method comprises an FIV p24 protein, or an immunogenic fragment thereof. In a specific embodiment, at least one immunogen is an FIV peptide of the invention comprising an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46.

The subject invention also concerns FIV peptides representing epitopes conserved with primate immunodeficiency viruses, such as HIV and SIV. In one embodiment, the FIV peptide comprises an amino acid sequence from an FIV p24 protein, or an immunogenic fragment or variant thereof. In a specific embodiment, the FIV p24 protein is an $FIV_{BANG}$, $FIV_{SHI}$, or $FIV_{FC1}$ p24 protein. In an exemplified embodiment, an FIV peptide of the invention has an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46.

The subject invention also concerns HIV peptides representing epitopes conserved with feline immunodeficiency viruses. In one embodiment, the HIV peptide comprises an amino acid sequence from an HIV p24 protein, or an immunogenic fragment or variant thereof. In a specific embodiment, the HIV p24 protein is an HIV-1$_{UCD1}$ or an HIV-1$_{LAI/LAV}$ p24 protein. In an exemplified embodiment, an HIV peptide of the invention has an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39.

Immunogens of the invention are typically administered parenterally, by injection, for example, either subcutaneously, intraperitoneally, or intramuscularly. Other suitable modes of administration include oral or nasal administration. Usually, the immunogens are administered to a human or other animal at least two times, with an interval of one or more weeks between each administration. However, other regimens for the initial and booster administrations of the immunogens are contemplated, and may depend on the judgment of the practitioner and the patient being treated.

Immunogenic compositions of the subject invention can be prepared by procedures well known in the art. For example, the immunogens are typically prepared as injectables, e.g., liquid solutions or suspensions. The immunogens are administered in a manner that is compatible with dosage formulation, and in such amount as will be therapeutically effective and immunogenic in the recipient. The optimal dosages and administration patterns for a particular immunogens formulation can be readily determined by a person skilled in the art.

Immunogens that can be used in accordance with the present invention can be provided with a pharmaceutically-acceptable carrier or diluent. In one embodiment, an immunogen of the invention is provided with one or more adjuvants that increase the human or animal's immune response against the immunogen. Immunogens of the invention can be provided with and/or administered with any suitable adjuvant or adjuvants known in the art.

The subject invention also concerns compositions comprising an immunogen of the invention derived from a primate immunodeficiency virus and a feline or human cytokine or lymphokine. The immunogen can be from HIV, including HIV-1, e.g., HIV-1$_{IIIB}$, HIV-1$_{LAI/LAV}$, HIV-1$_{UCD1}$, and HIV-1$_{BRU}$, and HIV-2. HIV immunogens of the composition include, but are not limited to, HIV gp160, gp120, gp41, p24, p31, p17, p7 or a protein encoded by an HIV gag, pol, env, tat, rev, nef, vif, vpr, vpu, or vpx genes, or a fragment or variant thereof. In a specific embodiment, an HIV peptide of the invention has an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In one embodiment, the lymphokine is feline or human IL-12, IL-15, and/or IL-18. In an exemplified embodiment, the immunogen is HIV-1 p24 and the lymphokine is feline IL-18. Compositions can also include an adjuvant, such as one of the adjuvants described herein.

The subject invention also concerns compositions comprising an immunogen of the invention derived from a feline immunodeficiency virus and a feline or human cytokine or lymphokine. The immunogen can be from any subtype or strain of FIV, including $FIV_{Pet}$, $FIV_{Bang}$, and $FIV_{Shi}$. FIV immunogens of the composition include, but are not limited to, FIV gp160, gp120, gp41, p24, p31, p17, p7 or a protein encoded by an FIV gag, pol, env, tat, rev, nef, vif, vpr, vpu, or vpx genes, or a fragment or variant thereof. In a specific embodiment, an FIV peptide of the invention has an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46. In one embodiment, the lymphokine is feline or human IL-12, IL-15, and/or IL-18. In a specific embodiment, the immunogen is FIV-1 p24 and the lymphokine is human IL-18. Compositions can also include an adjuvant, such as one of the adjuvants described herein.

The subject invention also concerns kits and dosage formulations comprising in one or more containers an immunogen of the invention derived from a primate immunodeficiency virus and a feline or human cytokine or lymphokine. The immunogen can be from HIV, including HIV-1, e.g., HIV-1$_{IIIB}$, HIV-1$_{LAI/LAV}$, HIV-1$_{UCD1}$, and HIV-1$_{BRU}$, and HIV-2. HIV immunogens of the composition include, but are not limited to, HIV gp160, gp120, gp41, p24, p31, or a protein encoded by an HIV gag, pol, env, tat, rev, nef, vif, vpr, vpu, or vpx gene, or an immunogenic fragment or variant thereof. In an exemplified embodiment, an HIV peptide of the invention has an amino acid sequence shown in any of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39, or an immunogenic fragment or variant of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 39. In one embodiment, the lymphokine is feline or human IL-12, IL-15, and/or IL-18. In an exemplified embodiment, the immunogen is HIV-1 p24 and the lymphokine is feline IL-18. Kits and dosage formulations can also include an adjuvant, such as one of the adjuvants described herein.

The subject invention also concerns kits and dosage formulations comprising in one or more containers an immunogen of the invention derived from a feline immunodeficiency virus and a feline or human cytokine or lymphokine. The immunogen can be from any subtype or strain of FIV, including $FIV_{Pet}$, $FIV_{Bang}$, and $FIV_{Shi}$. FIV immunogens of the composition include, but are not limited to, FIV gp160, gp120, gp41, p24, p31, p17, p7, or a protein encoded by an FIV gag, pol, env, tat, rev, nef, vif, vpr, vpu, or vpx gene, or an immunogenic fragment or variant thereof. In an exemplified embodiment, an FIV peptide of the invention has an amino acid sequence shown in any of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46, or an immunogenic fragment or variant of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 41, SEQ ID NO: 42, SEQ ID NO: 43, SEQ ID NO: 44, SEQ ID NO: 45, or SEQ ID NO: 46. In one embodiment, the lymphokine is feline or human IL-12, IL-15, and/or IL-18. In a specific embodiment, the immunogen is FIV p24 and the lymphokine is human IL-18. Kits and dosage formulations can also include an adjuvant, such as one of the adjuvants described herein.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or 1 to 3 amino acids removed from, either or both ends of the disclosed peptides using standard techniques known in the art. Preferably, any added amino acids would be the same as the corresponding amino acids of the full-length protein from which the peptide is derived. The skilled artisan, having the benefit of the teachings disclosed in the subject application, could easily determine whether a longer or shorter peptide retained the immunogenic activity of the specific peptides exemplified herein.

Substitution of amino acids other than those specifically exemplified or naturally present in a peptide of the invention are also contemplated within the scope of the present invention. For example, non-natural amino acids can be substituted for the amino acids of a peptide, so long as the peptide having the substituted amino acids retains substantially the same immunogenic activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide of the present invention having an amino acid of one class is replaced with another amino acid of the same class fall within the scope of the subject invention so long as the peptide having the substitution still retains substantially the same immunogenic activity as the peptide that does not have the substitution. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Polynucleotides encoding a specifically exemplified peptide of the invention, or a shorter or longer peptide, or a peptide having one or more amino acid substitutions in the sequence are contemplated within the scope of the present invention. The subject invention also concerns variants of the polynucleotides of the present invention that encode a peptide of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a peptide of the present invention can be generated as described herein and tested for the presence of immunogenic activity using standard techniques known in the art.

Polynucleotides and peptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See Worldwide Website: ncbi.nlm.nih.gov.

All patents, patent applications, provisional applications, and publications referred to or cited herein are incorporated by reference in their entirety to the extent they are not inconsistent with the explicit teachings of this specification.

MATERIALS AND METHODS FOR EXAMPLES 2 TO 5

Vaccine Efficacy of Studies 1-4.

Four separate studies were performed to evaluate the protective efficacy of HIV-1 p24 vaccine against $FIV_{Bang}$ and $FIV_{FC1}$ strains in cats (Table 2, Studies 1-4). $FIV_{FC1}$ belongs to subtype B and $FIV_{Bang}$ is a recombinant of subtype $A_{gag,pol,env(V1-V3)}$ and subtype $B_{env(V4-V9)}$ (Pu et al., 2005). The p24 from subtype B HIV-1 (HIV-$1_{UCD1}$ or HIV-$1_{LAI/LAV}$) that cross-reacted strongly with sera from dual-subtype FIV vaccinated cats was used as vaccine immunogen (Pu et al., 2001). The HIV-1 p24 vaccine consisted of recombinant p24 (200-250 µg) of HIV-$1_{UCD1}$ or HIV-$1_{LAI/LAV}$ mixed in modified Ribi adjuvant (Corixa Corporation, Hamilton, Mont.) (1 ml/dose) containing recombinant human interleukin-12 (rHuIL-12, Genetics Institute, Cambridge, Mass.; 5 µg/dose) (Ribi/rHuIL-12), recombinant feline IL-18 (rFeIL-18; 5 µg/dose) (Ribi/rFeIL-18), or without cytokine (Ribi). The modified Ribi adjuvant (modification of Corixa's Ribi R-730) contained cell wall skeleton (25 µg/dose) (Corixa Corporation. Ribi Adjuvant System (RAS) research adjuvant fact sheet. http://www.corixa.com/ras.pdf) and *E. coli* M15 lipopolysaccharide (5-50 EU/dose) as our approach to enhance toll-receptor recognition (Reis e Sousa, 2004). In Study 1, the cats were immunized with either HIV-$1_{UCD1}$ p24 in Ribi/rHuIL-12 (Group 1), HIV-$1_{LAI/LAV}$ p24 in Ribi/rHuIL-12 (Group 2), HIV-$1_{UCD1}$ p24 in Ribi (Group 3), or Ribi alone (Group 4). In Study 2, the cats were immunized with either HIV-$1_{LAI/LAV}$ p24 in Ribi/rHuIL-12 (Group 1), $FIV_{Bang}$ p24 in Ribi/rHuIL-12 (Group 2), $FIV_{Pet/Shi}$ p24 in Ribi/rHuIL-12 (Group 3), or Ribi/rHuIL-12 (Group 4). In Study 3, the cats were immunized with HIV-$1_{UCD1}$ p24 in Ribi/rFeIL-18 (Group 1) or Ribi (Group 2); and the control cats were immunized with Ribi/rFeIL-18, Ribi, or PBS (Group 3). In Study 4, the cats were immunized with HIV-$1_{UCD1}$ p24 in Ribi/rHuIL-12 (Group 1) or with PBS (Group 2). These studies with individual groups are shown in Table 2.

All cats were challenged intravenously with 15 median cat infectious dose ($CID_{50}$) of inoculum consisting of either pooled $FIV_{Bang}$-infected plasma (Studies 1-3) or pooled $FIV_{FC1}$-infected peripheral blood mononuclear cells (PBMC) (Study 4) derived directly from infected animals (Pu et al., 2001). Infection status of the cats was monitored by virus isolation based on RT activity and proviral PCR performed on the PBMC collected every 3-4 weeks post-inoculation (wpi) and on the lymph node (LN) and bone marrow (BM) cells at 18 or 24 wpi as previously described (Pu et al., 2001) or at 33-34 and 52 wpi. Cats were considered FIV negative by the absence of detectable virus, virus neutralizing (VN) antibodies, and immunoblot antibodies to FIV (nucleoprotein/matrix [p10/p15], polymerase [p65, p50], transmembrane envelope [gp40], and surface envelope [gp95]) at 1:50 and 1:250 serum dilutions (Pu et al., 2001). Immunoblot analysis was also used to detect cross-reactive antibodies to FIV core p24. All cats were monitored for 18 or 24 wpi, except for the vaccinated/protected cats from Studies 1, 3, and 4, which were monitored until 52 wpi.

Vaccine Immunogenicity

The $FIV_{Bang}$ p24 reactivity of the antibodies from vaccine-immunized cats and adjuvant/PBS-immunized controls were determined by immunoblot analysis using $FIV_{Bang}$ p24 as a substrate. The cross-reactive specificity of these antibodies (1:200 serum dilution) was determined by ELISA analysis (Yamomoto et al., 1993) using overlapping 28-30mer peptides of $FIV_{Bang}$ p24 as substrates. Only those reactivities that are 3-fold the pre-immunization/pre-infection sera were considered positive reactivity. The FIV/HIV-1 specific cellular immune responses were determined by feline interferon-γ (FeIFNγ) ELISpot of dendritic cell (DC)-primed PBMC from vaccine-immunized and PBS-immunized cats. Briefly, plastic adherent BM cells were cultured in RPMI media containing recombinant feline granulocyte-macrophage colony-stimulating factor (50 ng/ml; R&D Systems, Minneapolis, Minn.) and rFeIL-4 (25 ng/ml) produced according to a previously described method (Lerner et al., 1997; Wondimu et al., 2001). On culture day 10, the non-adherent fraction was re-cultured for additional 2 days in RPMI media containing recombinant human tumor necrosis factor-α (50 ng/ml, R&D Systems), to induce maturation (Weigel et al., 2002). The mature DCs were then incubated with peptide (2 μg/0.2 μl/well) in 96 round-bottom wells ($2 \times 10^4$ cells/well) for 18 hr and transferred to 96-well FeIFNγ ELISpot plates containing $2 \times 10^5$ autologous PBMC. ELISpot plates were processed according to manufacturer's method (R&D Systems) and analyzed with an ELISpot reader (MVS Pacific, LLC, Minneapolis, Minn.).

Sequencing, Expression, and Purification of HIV-1 p24, FIV p24, and FeIL-18

The proviral genes of HIV-1$_{LAI/LAV}$ (kindly provided by Dr. Francious Barre-Sinoussi, Pasteur Institute, France; NCBI accession #K02013), HIV-1$_{UCD1}$ (isolated from an HIV-positive individual from San Diego, Calif.; NCBI #AY679786), $FIV_{Bang}$ (NCBI #AY684181), $FIV_{Pet}$ (NCBI #NC001482), and $FIV_{Shi}$ (NCBI #D37818; #AY679785) were used to derive the viral p24 proteins. The whole gag sequence was obtained by PCR amplification of proviral DNA from HIV-1$_{UCD1}$- or HIV-1$_{LAI/LAV}$-infected HuT-78 cells, and cloned into pCR2.1 vector (TA cloning kit, Invitrogen, Carlsbad, Calif.). Three to eight clones were used for sequence confirmation. The HIV-1$_{LAI/LAV}$ p24 sequence was identical to the reported HIV-1$_{HXB2}$ p24 sequence (NCBI #K03455) and differed from HIV-1$_{UCD1}$ by eight aa. The confirmed sequence of p24 gene was subcloned into pQE30 for expression in *E. coli* M15[pREP4] (QIAexpressionist, Qiagen Inc., Valencia, Calif.). Recombinant p24 product was purified on Ni-NTA resin using the manufacturer's protocol. Purity of the product was >97% as determined by silver stain analysis on SDS-PAGE. The specificity of the product was determined by immunoblot analysis using human and feline polyclonal antibodies reactive to either HIV-1 or FIV p24, respectively.

The rFeIL-18 was produced from *E. coli* expression system using a previously described method with modification (Ishizaka et al., 2001; Salek-Ardakani et al., 2002). The FeIL-18 sequence was obtained by RT-PCR amplification of mRNA from feline splenocytes. Amplified products were cloned into pCR2.1 vector for sequence confirmation based on published FeIL-18 sequence (Ishizaka et al., 2001). The confirmed sequence was subcloned into pMAL-c2G (New England Biolabs, Inc., Beverly, Mass.) for expression in *E. coli* ER2508 strain as a fusion protein (FeIL-18 fused to maltose-binding protein). The fusion protein was cleaved with Genenase I and the cleaved product was purified by amylose resin chromatography using the manufacturer's protocol (New England Biolabs, Inc.). Purity of the product was determined by silver stain analysis. Biological activity of the rFeIL-18 was determined by proliferation-based IL-18 bioassay using PBMC instead of spleen cells (Gaucher et al., 2003).

Statistical Analyses

Individual immunization groups in each study (Table 2) and combined groups from different studies (Table 3) were analyzed for statistical significant difference by analysis of variance (ANOVA). Comparisons that demonstrated overall significance by ANOVA were evaluated by two-way paired T-test (SAS program, version 8.0) and were considered to have statistical difference when $p<0.05$.

Following are examples which illustrate procedures for practicing the subject invention. These examples should not be construed as limiting. All percentages are by weight and all solvent mixture proportions are by volume unless otherwise noted.

EXAMPLE 1

FIV Challenge Studies

Four SPF cats each (n=4) were immunized four times with either HIV-1 vaccine formulation A or HIV-1 vaccine formulation B at 3 week intervals and challenged 3 weeks after the last boost with 15 cat infectious doses ($CID_{50}$) of in vivo-derived $FIV_{Bangston}$ innoculum. Additional four SPF cats (control group) received no immunization but were similarly challenged with FIV. HIV-1 vaccine formulation A consisted of 200 μg of HIV-1$_{UCD1}$ p24, 25 μg of HIV-1$_{IIIB}$ gp120 (ImmunoDiagnostics Inc., Woburn, Mass.), and 25 μg of HIV-1$_{IIIB}$ gp160 (ImmunoDiagnostics Inc.) mixed in 0.5 ml of Ribi Adjuvant System comprising the cell wall skeleton (CWS) component (25 μg/dose cell wall skeleton)(Corixa Corp., Seattle, Wash.) containing 5 μg of recombinant human interleukin-12 (rHuIL-12). HIV-1 vaccine formulation B consisted of 200 μg of HIV-1$_{UCD1}$ p24 mixed in 0.5 ml of Ribi Adjuvant System CWS component containing 5 μg of rHuIL-12. Recombinant HIV-1$_{UCD1}$ p24 was produced in an *E. coli* expression system using QIAexpress pQE vector (Qiagen Inc., Valencia, Calif.) and the expressed 6×His-tagged p24 product was purified by Ni-NTA affinity chromatography (Qiagen Inc.). In vivo-derived FIV innoculum consisted of pooled plasma from two $FIV_{Bangston}$-infected cats which was titrated in vivo using groups of 3-4 SPF cats per $\log_{10}$ dilution (Pu et al., 2001).

Results of this study are shown in Table 1. As an additional method of determining FIV infection status, virus isolation was performed using both reverse transcriptase (RT) assay with proviral PCR as virus detection systems. One of four (1/4) cats immunized with HIV-1 vaccine formulation A and two of four (2/4) cats immunized with HIV-1 vaccine formulation B and subsequently challenged with FIV were negative for FIV by virus isolate, lost antibodies to FIV p24 and developed no antibodies to FIV gp95 at 16 weeks post challenge, while the remaining cats developed antibodies to FIV gp95 and developed persistently stronger antibody responses to FIV p24. All four control cats developed antibodies to both FIV p24 and gp95 by 16 weeks post challenge and virus isolation positive for FIV by 13 weeks post challenge. Hence, HIV-1 vaccine formulation B (HIV-1 p24 alone) appeared to have better or equivalent efficacy at protecting cats against FIV challenge than HIV-1 vaccine formulation A, suggesting that HIV-1$_{UCD1}$ p24 is a vaccine component that can induce protective immunity against FIV challenge. All four cats immunized with HIV-1 vaccine formulation A and three of four cats immunized with HIV-1 vaccine formulation B developed cross-reactive antibodies to FIV p24 after the fourth (4th) vaccination.

Since there were no cross-reactive antibodies to FIV gp95 in HIV-1 vaccinated cats that exhibited a protective immune response to FIV, the absence or presence of antibodies to FIV gp95 was indicative of whether an animal had been vaccinated with HIV or infected with FIV, respectively. In addition, the loss of cross-reactive antibodies to FIV p24 in vaccinated cats by the end of the study was also indicative that the vaccinated animals were protected from FIV challenge.

EXAMPLE 2

Challenge Efficacy Studies

In Study 1 (Table 2), all four cats (100%, Group 1) vaccinated with HIV-1$_{UCD1}$ p24 in Ribi/rHuIL-12 were protected against FIV$_{Bang}$ challenge that infected all three control cats (Group 4). In contrast, only two of four cats (50%, Group 2) vaccinated with HIV-1$_{LAI/LAV}$ p24 in Ribi/rHuIL-12, and one of three cats (33%, Group 3) vaccinated with HIV-1$_{UCD1}$ p24 in Ribi were protected. Statistically significant difference was only observed between the protection rates of Groups 1 and 4 ($p<0.01$). All vaccinated/protected cats in Study 1 remained negative for FIV infection even at 52 wpi. In Study 2, all three cats (100%, Group 1) vaccinated with HIV-1$_{LAI/LAV}$ p24 in Ribi/rHuIL-12 were protected, while all three Ribi/rHuIL-12-immunized cats (Group 4) were infected. However, only one of three FIV$_{Bang}$ p24-vaccinated cats (33%, Group 2) and two of three FIV$_{Pet/Shi}$ p24-vaccinated cats (67%, Group 3) were protected.

Figure 1B:
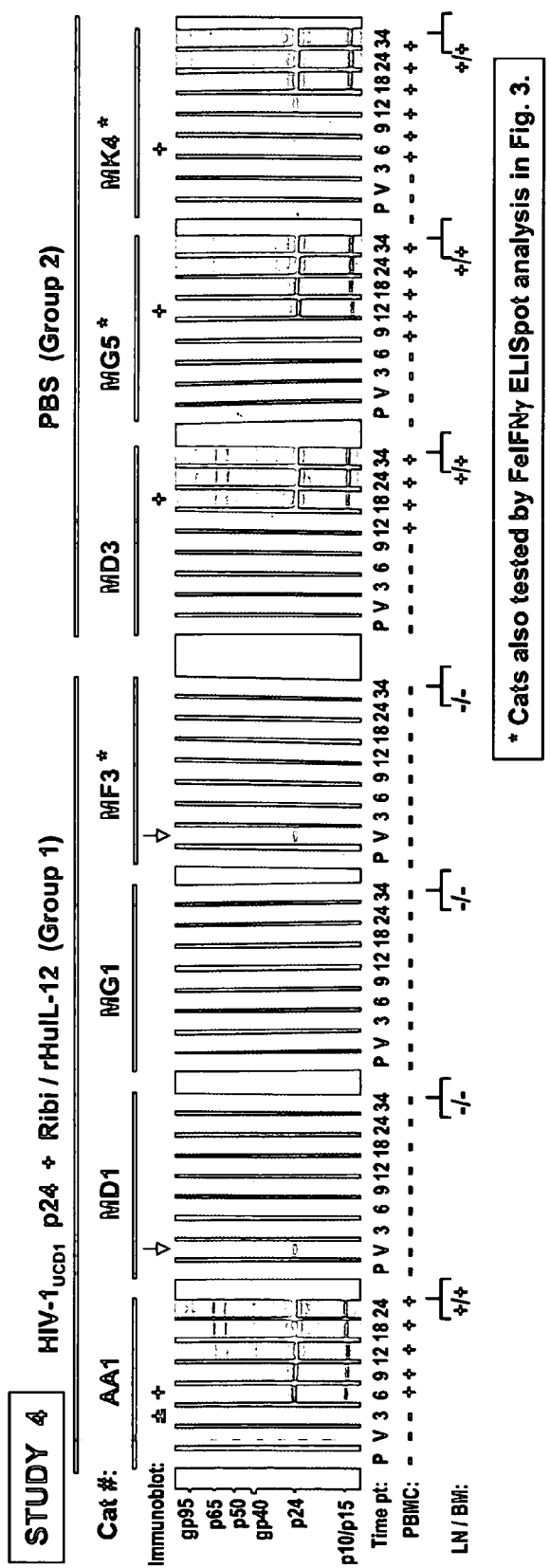

Using a different T-helper 1 cell (Th1)-promoting cytokine adjuvant, in Study 3, two of three cats (67%, Group 1) vaccinated with HIV-1$_{UCD1}$ p24 mixed in Ribi/rFeIL-18 were protected (FIG. 1, Table 2), while all six control cats (Group 3) were infected (typical results from three cats shown, FIG. 1; Table 2). Like Studies 1 and 2, protection was demonstrated by negative virus isolation of tissues (PBMC, LN, BM) and by the absence of FIV antibody development until 52 wpi (FIG. 1). Again, only one of three cats (33%, Group 2) vaccinated with HIV-1$_{UCD1}$ p24 in Ribi was protected, similar to the observation in Study 1 that showed HIV-1 p24 formulated in Ribi/rHuIL-12 to be more effective than those formulated in only Ribi (Table 2). In order to determine whether HIV-1 p24 protection is effective against challenge strains distinctly different from the subtype A gag of FIV$_{Bang}$, HIV-1$_{UCD1}$ p24-vaccinated cats were challenged with subtype B FIV$_{FC1}$ in Study 4 (FIG. 1, Study 4; Table 2). Three of four cats (75%, Group 1) vaccinated with HIV-1$_{UCD1}$ p24 in Ribi/rHuIL-12 were protected (FIV-negative even at 52 wpi) against FIV$_{FC1}$ challenge that infected all three control cats (Group 2). These observations demonstrate the protective efficacy of subtype B HIV-1 p24 against FIV strains containing distinct subtype A and B gag domains. Furthermore, analysis of the vaccinated/unprotected cats of Studies 3 and 4 (FIG. 1) indicates that none of these cats had enhancement in FIV infection.

EXAMPLE 3

Cross-Reactive Antibodies to FIV P24

ELISA- and immunoblot-antibody titers to HIV-1 and FIV p24 proteins in Studies 1-4 increased with each HIV-1 p24 immunization (only immunoblot results shown, FIG. 2A). Thirteen of fifteen (87%; 12 ELISA positive, FIG. 3A; 13 immunoblot positive, data not shown) vaccinated/protected cats tested and six of eight (75%, data not shown) vaccinated/unprotected cats developed either ELISA or immunoblot antibodies to FIV p24 after 3rd vaccination before challenge. The protected cats were negative for antibodies to FIV transmembrane peptide, TM695-705 (FIG. 3A), while all five FIV-infected cats were positive for antibodies to TM(695-705). These results suggest that the development of cross-reactive antibodies to FIV p24 protein does not correlate with vaccine protection. Furthermore, no VN antibodies to FIV subtype A, B, and D strains were detected in the cats with either HIV-1 or FIV p24 vaccination (data not shown). In contrast, the sera from cats immunized with commercial whole-virus FIV$_{Pet/Shi}$ vaccine (Fel-O-Vax® FIV, Fort Dodge Animal Health, Fort Dodge, Iowa) had moderate titers of VN antibodies to FIV$_{Pet}$ and FIV$_{Shi}$ but only weak VN titers to FIV$_{Bang}$ and FIV$_{FC1}$.

EXAMPLE 4

Sequence and B-Cell Epitope Analyses

The HIV-1$_{LAI/LAV}$ p24 sequence was identical to the reported HIV-1$_{HXB2}$ p24 sequence (NCBI #K03455) and differed from HIV-1$_{UCD1}$ p24 by eight aa (FIG. 2B). Amino acid sequence comparisons between HIV-1$_{UCD1}$ p24 (231 aa) and either FIV$_{Bang}$ or FIV$_{FC1}$ p24 (223 aa) showed only 30.9% and 30.3% identity, respectively (FIG. 2B). Only regions toward the carboxyl-terminus contained relevant homology, consisting of four aa between HIV-1$_{UCD1}$ and FIV$_{Bang}$ (HIV-1 residues 210-213: TLEE) and seven aa between HIV-1$_{UCD1}$ and FIV$_{FC1}$ (HIV-1 residues 193-199: NANPDCK). Amino acid sequence comparisons between HIV-1$_{LAI/LAV}$ and either FIV$_{Bang}$ p24 or FIV$_{FC1}$ p24 exhibited 31.3% and 30.8% identity, respectively. The regions that had the longest identical sequence were the same as those observed between HIV-1$_{UCD1}$ and the two FIV strains. Overall, the carboxyl-terminal region contained more conservation between the HIV-1 and FIV p24 sequences. Sequence analysis of p24 from HIV-1$_{UCD1}$ and HIV-1$_{LAI/LAV}$ demonstrates seven of eight aa differences found at the amino-terminus (FIG. 2B). Based on antibody reactivity to overlapping 28-30mer peptides of FIV p24 (FIG. 3A), the antibodies produced by HIV-1$_{UCD1}$ p24-vaccinated cats before challenge reacted strongest with peptide FB4/71-100, moderately with peptide FB11/197-223, and minimally with peptides FB3/53-81, FB9/161-188, and FB10/178-207. Therefore, at least two cross-reactive B-cell epitopes are recognized by the antibodies that are induced by HIV-1 p24 vaccination. According to hydropathy plot analysis, the reactive peptides are in the hydrophilic regions, which generally contain the B-cell antigenic sites (data not shown). The pattern of cross-reactivity to FIV peptides (FB4/71-100 and FB11/197-223) with sera from HIV-1 p24-vaccinated cats is similar to the antibody reactivity of sera from FIV-infected cats (FIG. 3A). The presence of antibodies to peptides FB4/71-100 and FB11/197-223 did not correlate with vaccine protection, since protection was also achieved in HIV-1 p24-vaccinated cats that had no cross-reactive antibodies to these peptides. In fact, two vaccinated/protected cats developed no ELISA and immunoblot antibodies to FIV p24 protein and peptides.

EXAMPLE 5

Cellular Immune Analyses

A selected number of cats from Studies 3 and 4 were tested for cellular immune function (FeIFNγ ELISpot) after challenge and after demonstration of full protection at 33-34 wpi. Since the DC-priming was unavailable in our laboratory until recently, only three vaccinated/protected cats (#JB6 and #IW1, Study 3; #MF3, Study 4) and two infected control cats (#MK4 and #MG5, Study 4) were tested by FeIFNγ ELISpot analysis of the DC-primed PBMC. The PBMC from all three vaccinated/protected cats had strong FeIFNγ ELISpot responses to three FIV p24 peptides (F4.5/122-131, F6/155-164, F7/183-191) (≧baseline, FIG. 3B1). Two of these cats also responded to peptide F7.8/210-219. Furthermore, the PBMC from all three cats responded to the three counterpart HIV-1 p24 peptides (H4.5/130-140, H6/162-172, H7/191-199) and also to peptide H7.8/217-226 (≧baseline, FIG. 3B2). In contrast, the PBMC from infected control cat (#MK4) had only minimal FeIFNγ ELISpot responses to three FIV p24 peptides (F2/15-25, F7.8/210-219, F8/214-223) (≧baseline, FIG. 3B3), while the PBMC from another infected cat (#MG5) had no responses to any of the nine FIV p24 peptides (HIV-1 peptides not tested). Since these targeted peptides corresponded to HIV-1 sequences that are the reported CTL epitopes for HIV-1-positive individuals (Los Alamos National Laboratory. HIV Databases. Epitope maps. http://hiv-web.lanl.gov/content/immunology/maps/maps.h-tml/), we speculate that they may represent FIV-specific CTL epitopes. Future studies using separated $CD4^+$ and $CD8^+$ T-cell subpopulations from vaccinated cats will determine whether the responses are CTL, Th, or both.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

HIV-1 Protein Immunogenicity & Efficacy Against $FIV_{Bang}$ Challenge Infection (Study 1)

| Cat # | VACCINE: HIV-1 Immunogens (Adjuvants) | Pre | V3 | V4 | 4 wpc | 7 wpc | 10 wpc | 13 wpc | 16 wpc | HIV-1 Immunoblot (p24/gp120/160) Pre | V4 | 10 wpc | 13 wpc | 16 wpc | 18 wpc | FIV Status Summary |
|---|---|---|---|---|---|---|---|---|---|---|---|---|---|---|---|---|
| | Formulation A: | | | | | | | | | | | | | | | |
| L99 | HIV-1$_{UCD1}$ p24 + HIV- | −/− | −/H | +/H | ±/H | +/− | +/− | +/− | +/+ | −/− | +/+ | + | + | + | + | + |
| 808 | 1$_{IIIB}$ gp120/160 | −/− | ++/H | ++/H | +/H | +/− | +/− | +/− | +/+ | −/− | +/+ | + | + | + | + | + |
| 9QM | | −/− | +/H | +/H | ±/− | −/− | −/− | −/− | −/− | −/− | +/+ | − | − | − | − | − |
| 902 | (Ribi + IL-12) | −/− | +/H | ++/H | +/H | +/− | +/− | +/− | +/+ | −/− | +/+ | + | + | + | + | + |
| | Formulation B: | | | | | | | | | | | | | | | |
| K99 | | −/− | −/− | −/− | −/− | −/− | −/− | −/− | −/− | −/− | +/− | − | − | − | − | − |
| 806 | HIV-1$_{UCD1}$ p24 | −/− | −/− | +/− | ±/− | +/− | +/− | +/− | +/+ | −/− | +/− | + | + | + | + | + |
| 9QL | | −/− | +/− | +/− | +/− | −/− | −/− | −/− | −/− | −/− | +/− | − | − | − | − | − |
| 901 | (Ribi + IL-12) | −/− | −/− | +/− | +/− | ±/− | +/− | +/− | +/+ | −/− | +/− | + | + | + | + | + |
| M99 | | −/− | −/− | −/− | +/− | +/− | +/− | +/− | +/+ | −/− | ND | + | + | + | + | + |
| 811 | None | −/− | −/− | −/− | +/− | +/− | +/− | +/± | +/+ | −/− | ND | + | + | + | + | + |
| 9QN | | −/− | −/− | −/− | ±/− | +/− | ±/− | ±/− | +/+ | −/− | ND | − | + | + | + | + |
| 6DJ | | −/− | −/− | −/− | +/+ | ±/− | +/+ | +/+ | +/+ | −/− | ND | + | + | + | + | + |

Pre = pre-vaccination;
V3 = post-3rd vaccination;
V4 = post-4th vaccination.
4, 7, 10, 13, 16 & 18 wpc = 4, 7, 10, 13, 16 and 18 weeks post-challenge with FIV.
Negative (−/−) for antibodies to core p24 and envelope (FIV gp95; HIV gp120/160).
Positive for p24 antibodies but not for envelope antibodies (+/−).
Positive (+/+) for antibodies to core p24 and envelope.
H = antibodies to high molecular weight (p70) protein but no antibodies to FIV envelope (gp95).
ND = not determined

TABLE 2

Efficacy of HIV-1 p24 vaccine against FIV challenge.[a]

| Study-Group | Vaccine Immunogen (μg/dose) | Adjuvant | FIV Challenge (gag subtype) | # Protected/# Total[a] (p value)[b] |
|---|---|---|---|---|
| 1-1 | HIV-1$_{UCD1}$ p24 (250 μg) | Ribi/rHuIL-12 | Bang (A) | 4/4 (p < 0.01)[b] |
| 1-2 | HIV-1$_{LAI/LAV}$ p24 (250 μg) | Ribi/rHuIL-12 | Bang (A) | 2/4 |
| 1-3 | HIV-1$_{UCD1}$ p24 (250 μg) | Ribi | Bang (A) | 1/3 |
| 1-4 | None | Ribi | Bang (A) | 0/3 |
| 2-1 | HIV-1$_{LAI/LAV}$ p24 (200 μg) | Ribi/rHuIL-12 | Bang (A) | 3/3 |
| 2-2 | FIV$_{Bang}$ p24 (200 μg) | Ribi/rHuIL-12 | Bang (A) | 1/3 |
| 2-3 | FIV$_{Pet/Shi}$ p24 (200 μg) | Ribi/rHuIL-12 | Bang (A) | 2/3 |
| 2-4 | None | Ribi/rHuIL-12 | Bang (A) | 0/3 |
| 3-1 | HIV-1$_{UCD1}$ p24 (200 μg) | Ribi/rFeIL-18 | Bang (A) | 2/3 |
| 3-2 | HIV-1$_{UCD1}$ p24 (200 μg) | Ribi | Bang (A) | 1/3 |

TABLE 2-continued

Efficacy of HIV-1 p24 vaccine against FIV challenge.[a]

| Study-Group | (μg/dose) | Vaccine Immunogen Adjuvant | FIV Challenge (gag subtype) | # Protected/# Total[a] (p value)[b] |
|---|---|---|---|---|
| 3-3 | None | Ribi/rFeIL-18 or Ribi or PBS[c] | Bang (A) | 0/6 |
| 4-1 | HIV-1$_{UCD1}$ p24 (200 μg) | Ribi/rHuIL-12 | FC1 (B) | 3/4 |
| 4-2 | None | PBS | FC1 (B) | 0/3 |

Table 2 Footnotes:
[a]Detailed descriptions of the groups in Studies 1-4 are included in the Methods. The total number of cats in each study group is shown on the last column as # Total.
[b]Based on ANOVA, the protection rates between groups in only Study 1 had statistically significant differences. As a result, T-tests were performed between the protection rates of HIV-1 p24-vaccinated groups vs. the control group from Study 1 (i.e., Groups 1 vs. 4, Groups 2 vs. 4, Groups 3 vs. 4). Comparison between only Groups 1 and 4 had statistical significance and is shown with ($p < 0.01$) next to the protection rate.
[c]Two cats each were immunized with either Ribi/rFeIL-18 (n = 2), Ribi (n = 2), or PBS (n = 2).

TABLE 3

Summary of the combined protection rates from Studies 1-4.[a]

| Combined Group # | Study-Group Combined[a] | Vaccine Immunogen (μg/dose) | Adjuvant | # Protected/# Total (% Protection) | p-value[b] |
|---|---|---|---|---|---|
| A1 | 1-1, 1-2, 2-1, 3-1, 4-1 | HIV-1$_{UCD1}$ p24 & HIV-1$_{LAI/LAV}$ p24 | Ribi/rHuIL-12 or Ribi/rFeIL-18 | 14/18 (78%) | <0.001* |
| A2 | 1-4, 2-4, 3-3, 4-2 | None | Ribi/rHuIL-12 or Ribi/rFeIL-18 or Ribi or PBS | 0/15 | |
| B1 | 1-1, 3-1, 4-1 | HIV-1$_{UCD1}$ p24 | Ribi/rHuIL-12 or Ribi/rFeIL-18 | 9/11 (82%) | <0.001* |
| B2 | 1-4, 3-3, 4-2 | None | Ribi/rFeIL-18 or Ribi or PBS | 0/12 | |
| C1 | 1-2, 2-1 | HIV-1$_{LAI/LAV}$ p24 | Ribi/rHuIL-12 | 5/7 (71%) | <0.01* |
| C2 | 1-4, 2-4 | None | Ribi/rHuIL-12 or Ribi | 0/6 | |
| D1 | 1-3, 3-2 | HIV-1$_{UCD1}$ p24 | Ribi | 2/6 (33%) | 0.113 |
| D2 | 1-4, 3-3[c] | None | Ribi or PBS | 0/7 | |
| E1 | 2-2, 2-3 | FIV$_{Bang}$ p24 & FIV$_{Pet/Shi}$ p24 | Ribi/rHuIL-12 | 3/6 (50%) | 0.170 |
| E2 | 2-4 | None | Ribi/rHuIL-12 | 0/3 | |

Table 3 Footnotes:
[a]The combined protection rates and the statistical analyses performed on the combined groups from different studies are presented in Table 2. Only groups with similar vaccine formulations are combined. The first column shows the groups from different studies that were combined to obtain the different combined vaccinated groups and their corresponding combined control groups.
[b]By combining the groups with similar vaccine formulations, statistically significant differences were achieved between the protection rates of the vaccinated (HIV-1 p24/Ribi/cytokine, FIV p24/Ribi/rHuIL-12) groups and the corresponding combined control (PBS, Ribi, Ribi/cytokine) groups by ANOVA, but not all comparisons were statistically significant by two-way paired T-test. Based on paired T-test, statistical differences were observed between the protection rates of the combined Groups A1 vs. A2 ($p < 0.001$); Groups B1 vs. B2 ($p < 0.001$); and Groups C1 vs. C2 ($p < 0.01$); but not between Groups D1 vs. D2 ($p = 0.113$) and Groups E1 vs. E2 ($p = 0.170$). Furthermore, except for the comparisons between Groups A1 vs. D1 ($p = 0.048$) and Groups B1 vs. D1 ($p = 0.049$), there were no statistically significant differences amongst the protections rates of the different p24-vaccinated groups (i.e., Group A1 vs. Group B1 vs. Group C1 vs. Group D1 vs. Group E1), including comparisons between the protection rates of Groups A1 vs. E1 ($p = 0.211$) and Groups B1 vs. E1 ($p = 0.191$). Those comparisons with statistical significance at $p < 0.05$ are shown with (*).
[c]The protection rates of only Ribi-immunized (n = 2) and PBS-immunized (n = 2) cats in Study 3 were used (i.e., protection rate of Ribi/rFeIL-18-immunized cats not used). When the four Ribi/PBS-immunized cats from Study 3 are combined with the three Ribi-immunized cats from Study 1, the total number of control cats in Group D2 is seven (n = 7).

REFERENCES

U.S. Pat. No. 4,861,720
U.S. Pat. No. 5,037,753
U.S. Pat. No. 5,118,602
U.S. Pat. No. 5,275,813
U.S. Pat. No. 5,401,628
U.S. Pat. No. 5,510,106
U.S. Pat. No. 5,530,101
U.S. Pat. No. 5,565,319
U.S. Pat. No. 5,585,089
U.S. Pat. No. 5,693,762
U.S. Pat. No. 5,700,469
U.S. Pat. No. 5,763,160
U.S. Pat. No. 5,846,546
U.S. Pat. No. 5,846,825
U.S. Pat. No. 5,849,533
U.S. Pat. No. 6,180,370
U.S. Pat. No. 6,254,872
U.S. Pat. No. 6,407,213
U.S. Pat. No. 6,447,993
U.S. Pat. No. 6,500,623
U.S. Pat. No. 6,503,753
U.S. Published Patent Application No. 20010004531
U.S. Published Patent Application No. 20020032165
U.S. Published Patent Application No. 20020156037
U.S. Published Patent Application No. 20040009941
U.S. Published Patent Application No. 20040047878
U.S. Published Patent Application No. 20040076632

Abimiku, A. G., G. Franchini, J. Tartaglia, K. Aldrich, M. Myagkikh, P. D. Markham, et al. (1995) "HIV-1 recombinant poxvirus vaccine induces cross-protection against HIV-2 challenge in rhesus macaques," *Nat. Med.* 1:321-329.

Ackley, C. D., J. K. Yamamoto, N. B. Levy, N. C. Pedersen, M. D. Cooper (1990) "Immunologic abnormalities in pathogen-free cats experimentally infected with feline immunodeficiency virus," *J. Virol.* 64:5652-5655.

Altschul, S. F. et al. (1990) "Basic Local Alignment Search Tool," *J. Mol. Biol.* 215:402-410.

Altschul, S. F. et al. (1997) "Gapped BLAST and PSI-BLAST: A New Generation of Protein Database Search Programs," *Nucl. Acids Res.* 25:3389-3402.

Bottiger, B., A. Karlsson, P. A. Andreasson, A. Naucler, C. M. Costa, E. Norrby, et al. (1990) "Envelope cross-reactivity between human immunodeficiency virus type 1 and 2 detected by different serological methods: correlation between cross-neutralization and reactivity against the main neutralizing site," *J. Virol.* 64:3492-3499.

Byars, N E, A. C. Allison (1987) "Adjuvant formulation for use in vaccines to elicit both cell-mediated and humoral immunity," *Vaccine* 5:223-228.

Calarota, S. A., D. B. Weiner (2003) "Present status of human HIV vaccine development," *AIDS* 17 (suppl 4):S73-S84.

Cohen, J. (2003) "Vaccine results lose significance under scrutiny," *Science* 299:1495.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure," *Proc. Natl. Acad. Sci. USA* 84(21):7413-7417.

Gaucher, D., K. Chadee (2003) "Gerbil interleukin-18 and caspase-1: cloning, expression and characterization," *Gene* 307:159-166.

Greenberg, A. E., S. Z. Wiktor, K. M. DeCock, P. Smith, H. W. Jaffe, T. J. Dondero, Jr. (1996) "HIV-2 and natural protection against HIV-1 infection," *Science* 272:1959-1960.

Guyader, M., M. Emerman, P. Sonigo, F. Clavel, L. Montagnier, M. Alzon (1987) "Genome organization and transactivation of the human immunodeficiency virus type 2," *Nature* 326:662-669.

Henderson, D. A., L. L. Borio, J. M. Lane (2004) "Smallpox and vaccinia," In: *Vaccines, 4th Ed.* Plotkin S A, Orenstein W A (editors). Philadelphia: Elsevier Inc., pp. 123-153.

Hosie, M. J., O. Jarrett (1990) "Serological responses of cats to feline immunodeficiency virus," *AIDS* 4:215-220.

Ishizaka, T., A. Setoguchi, K. Masuda, K. Ohno, H. Tsujimoto (2001) "Molecular cloning of feline interferon-γ-inducing factor (interleukin-18) and its expression in various tissues," *Vet. Immunol. Immunopathol.* 79:209-218.

Kakinuma, S., K. Motokawa, T. Hohdatsu, J. K. Yamamoto, H. Koyama, H. Hashimoto (1995) "Nucleotide Sequence of Feline Immunodeficiency Virus: Classification of Japanese Isolates into Two Subtypes Which Are Distinct from Non-Japanese Subtypes," *J. Virol.* 69(6):3639-3646.

Karlin, S. and Altschul, S. F. (1990) "Methods for Assessing the Statistical Significance of Molecular Sequence Features by Using General Scoring Schemes," *Proc. Natl. Acad. Sci. USA* 87:2264-2268.

Karlin, S. and Altschul, S. F. (1993) "Applications and Statistics for Multiple High-Scoring Segments in Molecular Sequences," *Proc. Natl. Acad. Sci. USA* 90:5873-5877.

Lerner, D. L., J. H. Elder (1997) "Felis catus interleukin-4 mRNA," NCBI GenBank (accession U39634).

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) "Phylogenetic analysis of gag genes from 70 international HIV-1 isolates provides evidence for multiple genotypes," *AIDS* 7:769-780.

Martin, E. W. (1995) *Remington's Pharmaceutical Science*, Easton Pa., Mack Publishing Company, 19$^{th}$ ed., 1995.

Matsuo, K., Y. Nishino, T. Kimura, R. Yamaguchi, A. Yamazaki, T. Mikami, et al. (1992) "Highly conserved epitope domain in major core protein p24 is structurally similar among human, simian and feline immunodeficiency viruses," *J. Gen. Virol.* 73:2445-2450.

McMichael, A. J., T. Hanke (2003) "HIV vaccines 1983-2003," *Nat. Med.* 9:874-880.

Merrifield, R. B. (1963) "Solid Phase Peptide Synthesis. I. The Synthesis of a Tetrapeptide" *J. Amer. Chem. Soc.* 85:2149-2156.

Murphy, F., D. W. Kingsbury (1990) "Virus Taxonomy," In *Fields Virology*, 2nd Ed., B. N. Fields, D. M. Knipe et al., eds, Raven Press, New York, Chapter 2, pp. 9-36.

Murphy, F. A. (1996) "Virus Taxonomy," In: *Fundamental Virology*, 3rd Ed. Fields B N, Knipe D M, P M Howley P M (editors). Philadelphia: Lippincott, Raven Publishers, pp. 15-57.

Nath, M. D., D. L. Peterson (2001) "In vitro assembly of feline immunodeficiency virus capsid protein: biological role of conserved cysteines," *Arch. Biochem. Biophys.* 392:287-294.

Nixon, D. F., J. Rthbard, M. P. Kieny, M. Delchambre, C. Thiriart, C. R. Rizza, et al. (1990) "An HIV-1 and HIV-2 cross-reactive cytotoxic T-cell epitope," *AIDS* 4:841-845.

Norrgren, H., S. Andersson, A. J. Biague, Z. J. da Silva, F. Dias, A. Naucler, et al. (1999) "Trends and interaction of HIV-1 and HIV-2 in Guinea-Bissau, West Africa: no protection of HIV-2 against HIV-1 infection," *AIDS* 13:701-707.

Olmsted, R. A., A. K. Barnes, J. K. Yamamoto, V. M. Hirsch, R. H. Purcell, P. R. Johnson (1989a) "Molecular cloning of feline immunodeficiency virus," *Proc. Nat. Acad. Sci. USA* 86:2448-2452.

Olmsted, R. A., V. M. Hirsch, R. H. Purcell, P. R. Johnson (1989b) "Nucleotide sequence analysis of feline immunodeficiency virus: Genome organization and relationship to other lentivirus," *Proc. Natl. Acad. Sci. USA* 86:8088-8092.

Pedersen, N. C., E. W. Ho, M. L. Brown, J. K. Yamamoto (1987) "Isolation of a T-lymphotropic virus from domestic cats with an immunodeficiency-like syndrome," *Science* 235:790-793.

Posnett, D. N. et al. (1988) "A Novel Method for Producing Anti-peptide Antibodies," *J. Biol. Chem.* 263(4):1719-1725.

Pu R., J. Coleman, J. Coisman, E. Sato, T. Tanabe, M. Arai, J. K. Yamamoto (2005) "Dual-subtype FIV vaccine (Fel-O-Vax® FIV) protection against heterologous subtype B FIV isolate," *Journal of Feline Medicine & Surgery* 7(1):65-70.

Pu, R., E. Sato, F. Sasaki, J. Coleman, M. Arai, J. K. Yamamoto (2002) "FIV antigens induce potent cross-reactive immunity to HIV-1," *Experimental Biology* 2002. New Orleans, April 2002 [FASEB Journal, p. A298, Abstract No. 237.21].

Pu, R., J. Coleman, M. Omori, M. Arai, T. Hohdatsu, C. Huang, et al. (2001) "Dual-subtype FIV vaccine protects cats against in vivo swarms of both homologous and heterologous subtype FIV isolates," *AIDS* 15:1225-1237.

Pu, R., J. Coleman, M. Omori, M. Mison, C. Huang, M. Arai, T. Tanabe, J. K. Yamamoto (2001) "Dual-subtype FIV vaccine protects cats against in vivo swarms of both homologous and heterologous subtype FIV isolates," *AIDS* 15:1-13.

Reis e Sousa, C. (2004) "Toll-like receptors and dendritic cells: for whom the bug tolls," *Semin. Immunol.* 16:27-34.

Rigby, M. A., E. C. Holmes, M. Pistello, A. Mackay, A. J. Leigh-Brown, J. C. Neil (1993) "Evolution of structural proteins of feline immunodeficiency virus: molecular epidemiology and evidence of selection for change," *J. Gen. Virol.* 74:425-436.

Robert-Guroff, M., K. Aldrich, R. Muldoon, T. L. Stern, G. P. Bansal, T. J. Matthews, et al. (1992) "Cross-neutralization of human immunodeficiency virus type 1 and 2 and simian immunodeficiency virus isolates," *J. Virol.* 66:3602-3608.

Rowland-Jones, S., J. Sutton, K. Ariyoshi, T. Dong, F. Gotch, S. McAdam, et al. (1995) "HIV-specific cytotoxic T-cells in HIV-exposed but uninfected Gambian women," *Nat. Med.* 1:59-64.

Salek-Ardakani, S., A. D. Stuart, J. E. Arrand, S. Lyons, J. R. Arrand, M. Mackett (2002) "High level expression and purification of the Epstein-Barr virus encoded cytokine viral interleukin 10: efficient removal of endotoxin," *Cytokine* 17:1-13.

Schim van der Loeff, M. F., P. Aaby, K. Aryioshi, T. Vincent, A. A. Awasana, C. Da Costa et al. (2001) "HIV-2 infection does not protect against HIV-1 infection in a rural community in Guinea-Bissau," *AIDS* 15:2303-2310.

Sodora, D. L., E. G. Shpaer, B. E. Kitchell, S. W. Dow, E. A. Hoover, J. I. Mullins (1994) "Identification of three feline immunodeficiency virus (FIV) env gene subtype and comparison of the FIV and human immunodeficiency virus type 1 evolutionary patterns," *J. Virol.* 68:2230-2238.

Talbott, R. L., E. E. Sparger, K. M. Lovelace, W. M. Fitch, N. C. Pedersen, P. A. Luciw, J. H. Elder (1989) "Nucleotide sequence and genomic organization of feline immunodeficiency virus," *Proc. Natl. Acad. Sci. USA* 86:5743-5747.

Tam, J. P. (1988) "Synthetic Peptide Vaccine Design: Synthesis and Properties of a High-Density Multiple Antigenic Peptide System," *Proc. Nat. Acad. Sci. USA* 85(15):5409-5413.

Tanabe, T., J. K. Yamamoto (2001) "Feline immunodeficiency virus lacks sensitivity to the antiviral activity of feline IFNγ," *J. Interferon Cytokine Res.* 21:1039-1046.

Travers, K., S. Mboup, R. Marlink, A. Gueye-Nidaye, T. Siby, I. Thior, et al. (1995) "Natural protection against HIV-1 infection provided by HIV-2," *Science* 268:1612-1615.

Uhl, E. W., R. Pu, T. Heaton-Jones, R. Pu, J. K. Yamamoto (2002) "FIV vaccine development and its importance to veterinary and human medicine: a review," *Vet. Immunol. Immunopath.* 90:113-132.

Weigel, B. J., N. Nath, P. A. Taylor, A. Panskaltsis-Mortari, W. Chen, A. M. Krieg, et al. (2002) "Comparative analysis of murine marrow-derived dendritic cells generated by Flt3L or GM-CSF/IL-4 and matured with immune stimulatory agents on the in vivo induction of antileukemia responses," *Blood* 100:4169-4176.

Whetter, L. E. et al. (1999) "Pathogenesis of simian immunodeficiency virus infection," *J. Gen. Virol.* 80:1557-1568.

Wondimu, A., M. Veit, B. Kohn, S. Kaul, A. Hoffmann, L. Brunnberg, et al. (2001) "Molecular cloning, expression and characterization of the *Canis familiaris* interleukin-4," *Cytokine* 16:88-92.

Yamamoto, J. K., B. A. Torres, R. Pu (2002) "Development of the dual-subtype FIV vaccine," *AIDScience* April 2002, 2(8), website at aidscience.org/Articles/ AIDScience020.asp/ Accessed 25 Dec. 2004.

Yamamoto, J. K., E. Sparger, E. W. Ho, P. H. Andersen, T. P. O'Connor, C. P. Mandell, L. Lowenstine, N. C. Pedersen (1988b) "Pathogenesis of experimentally induced feline immunodeficiency virus infection in cats," *Am. J. Vet. Res.* 49:1246-1258.

Yamamoto, J. K., N. C. Pedersen, E. W. Ho, T. Okuda, G. H. Theilen (1988a) "Feline immunodeficiency syndrome—a comparison between feline T-lymphotropic lentivirus and feline leukemia virus," *Leukemia*, December Supplement 2:204S-215S.

Yamamoto, J. K., T. Hohdatsu, R. A. Olmsted, R. Pu, H. Louie, H. Zochlinski, et al. (1993) "Experimental vaccine protection against homologous and heterologous strains of feline immunodeficiency virus," *J. Virol.* 67:601-605.

Yazbak, F. E., C. J. M. Diodati (2002) "Postpartum live virus vaccination: lessons from veterinary medicine," *Med. Hypoth.* 59:280-282.

Zvelebil, M. J., M. J. Sternberg, J. Cookson, A. R. Coats (1988) "Predictions of linear T-cell and B-cell epitopes in proteins encoded by HIV-1, HIV-2 and SIV$_{MAC}$ and the conservation of these sites between strains," *FEBS Lett* 242:9-21.

I claim:

1. A method for inducing or generating an immune response in a feline animal against a FIV protein, said method comprising administering to said animal an effective amount of at least one peptide of:
   i) a primate immunodeficiency virus protein, wherein said peptide comprises the amino acid sequence of SEQ ID NO: 12, or an immunogenic peptide having 1 to 15 additional amino acids added to either or both ends of the peptide of SEQ ID NO: 12, or an immunogenic peptide having 1 to 3 amino acids removed from either or both ends of the peptide of SEQ ID NO: 12.

2. The method according to claim 1, wherein said method further comprises administering an effective amount of an immunogen derived from a feline immunodeficiency virus (FIV) subsequent to the administration of said peptide.

3. The method according to claim 1, wherein said peptide is provided or administered with a pharmaceutically acceptable carrier or diluent.

4. The method according to claim 1, wherein said peptide is provided or administered with one or more adjuvants that increase the immune response of said animal against said peptide or said peptide is provided or administered with one or more cytokine or lymphokine.

5. The method according to claim 1, wherein said peptide is administered subcutaneously, intraperitoneally, intramuscularly, orally, or via nasal administration.

6. The method according to claim 4, wherein said adjuvant is selected from the group consisting of threonyl muramyl dipeptide (MDP), an oil-in-water emulsion containing detoxified endotoxin and mycobacterial cell wall components in squalene including cell wall skeleton (CWS), Freund's complete adjuvant, Freund's incomplete adjuvant, a lipopolysaceharide, alum, aluminum hydroxide, and saponin.

7. The method according to claim 4, wherein said cytokine or lymphokine is a feline cytokine or lymphokine.

8. The method according to claim 7, wherein said feline lymphokine is an interleukin.

9. The method according to claim 8, wherein said interleukin is selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22.

10. The method according to claim 1, wherein said FIV is a subtype A FIV or subtype B FIV.

\* \* \* \* \*

UNITED STATES PATENT AND TRADEMARK OFFICE
CERTIFICATE OF CORRECTION

PATENT NO. : 7,658,927 B2
APPLICATION NO. : 11/326062
DATED : February 9, 2010
INVENTOR(S) : Janet K. Yamamoto It is certified that error appears in the above-identified patent and that said Letters Patent is hereby corrected as shown below:

Column 28,
Line 15, "$FIV_{shi}$" should read --$FIV_{Shi}$--.

Column 29,
Table 1, Row Cat#808, "$1_{IIIB}gp120/160$" should read --$HIV-1_{IIIB}gp120/160$--.

Signed and Sealed this

Twenty-ninth Day of June, 2010

David J. Kappos
*Director of the United States Patent and Trademark Office*

SEQUENCE LISTING

```
<160> NUMBER OF SEQ ID NOS: 46

<210> SEQ ID NO 1
<211> LENGTH: 848
<212> TYPE: PRT
<213> ORGANISM: Human immunodeficiency virus type 1

<400> SEQUENCE: 1

Met Arg Val Lys Gly Ile Arg Lys Ser Phe Gln Tyr Leu Trp Arg Trp
1               5                   10                  15

Gly Ile Met Leu Leu Gly Met Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
```

-continued

```
            50                  55                  60
His Asn Val Trp Ala Thr His Ala Cys Val Pro Thr Asp Pro Ser Pro
 65                  70                  75                  80

Gln Glu Val Glu Leu Gln Asn Val Thr Glu Asp Phe Asn Met Trp Lys
                     85                  90                  95

Asn Asn Met Val Glu Gln Met His Glu Asp Val Ile Ser Leu Trp Asp
                    100                 105                 110

Gln Ser Leu Lys Pro Cys Val Lys Leu Thr Pro Leu Cys Val Thr Leu
                115                 120                 125

Asn Cys Thr Asp Leu Lys Asn Ala Thr Asn Thr Thr Ser Ser Ser Gly
130                 135                 140

Gly Gly Thr Met Glu Arg Gly Glu Ile Lys Asn Cys Ser Phe Lys Ile
145                 150                 155                 160

Thr Thr Asn Ile Arg Asn Lys Met Gln Lys Glu Tyr Ala Leu Phe Asp
                165                 170                 175

Lys His Asp Val Val Pro Ile Asp Lys Lys Asn Thr Arg Tyr Arg Leu
                180                 185                 190

Ile Ser Cys Asn Thr Ser Val Ile Thr Gln Ala Cys Pro Lys Val Ser
                195                 200                 205

Phe Glu Pro Ile Pro Ile His Phe Cys Ala Pro Ala Gly Phe Ala Ile
210                 215                 220

Leu Lys Cys Lys Asp Lys Lys Phe Asn Gly Lys Gly Ser Cys Thr Lys
225                 230                 235                 240

Val Ser Thr Val Gln Cys Thr His Gly Ile Arg Pro Val Val Ser Thr
                245                 250                 255

Gln Leu Leu Leu Asn Gly Ser Leu Ala Glu Glu Val Val Ile Arg
                260                 265                 270

Ser Asp Asn Phe Thr Asp Asn Ala Lys Thr Ile Ile Val Gln Leu Asn
                275                 280                 285

Glu Thr Val Glu Ile Asn Cys Thr Arg Pro Asn Asn Asn Thr Arg Lys
                290                 295                 300

Arg Ile Thr Met Gly Pro Gly Arg Val Phe Tyr Thr Thr Gly Glu Ile
305                 310                 315                 320

Ile Gly Asp Ile Arg Arg Ala His Cys Asn Ile Ser Gly Thr Lys Trp
                325                 330                 335

Asn Asn Thr Leu Lys Gln Ile Val Thr Lys Leu Arg Glu Lys Phe Gly
                340                 345                 350

Asn Lys Thr Ile Val Phe Lys Gln Ser Ser Gly Gly Asp Pro Glu Ile
                355                 360                 365

Val Met His Thr Phe Asn Cys Gly Gly Glu Phe Phe Tyr Cys Asn Thr
                370                 375                 380

Lys Gln Leu Phe Asn Ser Thr Trp Asn Asp Thr Asp Thr Leu Asn Asn
385                 390                 395                 400

Thr Glu Arg Ser Ser Lys Thr Ile Thr Leu Pro Cys Arg Ile Lys Gln
                405                 410                 415

Ile Ile Asn Met Trp Gln Glu Val Gly Lys Ala Met Tyr Ala Pro Pro
                420                 425                 430

Ile Ser Gly Gln Ile Arg Cys Ser Ser Asn Ile Thr Gly Leu Leu Leu
                435                 440                 445

Val Arg Asp Gly Gly Asn Asn Ala Glu Asn Glu Thr Glu Ile Leu Arg
                450                 455                 460

Pro Gly Gly Gly Asn Met Arg Asp Asn Trp Arg Ser Glu Leu Tyr Lys
465                 470                 475                 480
```

-continued

Tyr Lys Val Val Lys Ile Glu Pro Leu Gly Val Ala Pro Thr Lys Ala
            485                 490                 495
Lys Arg Arg Val Val Gln Arg Glu Lys Arg Ala Val Gly Thr Leu Gly
        500                 505                 510
Ala Leu Phe Leu Gly Phe Leu Gly Thr Ala Gly Ser Thr Met Gly Ala
    515                 520                 525
Ala Ser Met Ala Leu Thr Val Gln Ala Arg Gln Leu Leu Ser Gly Ile
    530                 535                 540
Val Gln Gln Gln Asn Asn Leu Leu Arg Ala Ile Glu Ala Gln Gln His
545                 550                 555                 560
Leu Leu Gln Leu Thr Val Trp Gly Ile Lys Gln Leu Gln Ala Arg Val
            565                 570                 575
Leu Ala Val Glu Arg Tyr Leu Lys Asp Gln Gln Leu Leu Gly Ile Trp
        580                 585                 590
Gly Cys Ser Gly Lys Phe Ile Cys Thr Thr Ala Val Pro Trp Asn Ala
    595                 600                 605
Ser Trp Ser Asn Lys Ser Leu Asp Lys Ile Trp Asn Asn Met Thr Trp
    610                 615                 620
Met Gln Trp Glu Arg Glu Ile Asp Asn Tyr Thr Asp Leu Ile Tyr Thr
625                 630                 635                 640
Leu Ile Glu Glu Ser Gln Asn Gln Gln Glu Lys Asn Glu Gln Glu Leu
            645                 650                 655
Leu Glu Leu Asp Lys Trp Ala Ser Leu Trp Asn Trp Phe Asp Ile Thr
        660                 665                 670
Lys Trp Leu Trp Tyr Ile Lys Ile Phe Ile Met Ile Val Gly Gly Leu
    675                 680                 685
Val Gly Leu Arg Ile Val Phe Ala Val Val Ser Ile Val Asn Arg Val
    690                 695                 700
Arg Gln Gly Tyr Ser Pro Leu Ser Phe Gln Thr His Phe Pro Ala Pro
705                 710                 715                 720
Arg Gly Pro Asp Arg Pro Glu Gly Ile Glu Glu Gly Gly Asp Arg
            725                 730                 735
Asp Arg Asp Arg Ser Ile Arg Leu Val Asp Gly Phe Leu Ala Leu Phe
        740                 745                 750
Trp Asp Asp Leu Arg Ser Leu Cys Leu Ser Ser Tyr His Arg Leu Arg
    755                 760                 765
Asp Leu Leu Leu Ile Val Thr Arg Ile Val Glu Leu Leu Gly Arg Arg
    770                 775                 780
Gly Trp Glu Ala Leu Lys Tyr Trp Trp Asn Leu Leu Gln Tyr Trp Ser
785                 790                 795                 800
Gln Glu Leu Lys Asn Ser Ala Ile Ser Leu Leu Asn Thr Thr Ala Ile
            805                 810                 815
Ala Val Ala Glu Gly Thr Asp Arg Val Ile Glu Val Gln Arg Ala
        820                 825                 830
Tyr Arg Ala Val Ile His Ile Pro Arg Arg Ile Arg Gln Gly Phe Glu
    835                 840                 845

<210> SEQ ID NO 2
<211> LENGTH: 499
<212> TYPE: PRT
<213> ORGANISM: Human immunodeficiency virus type 1

<400> SEQUENCE: 2

Met Gly Ala Arg Ala Ser Val Leu Ser Gly Gly Glu Leu Asp Lys Trp

```
1               5                   10                  15
Glu Lys Ile Arg Leu Arg Pro Gly Gly Lys Lys Tyr Lys Leu Lys
                20                  25                  30
His Ile Val Trp Ala Ser Arg Glu Leu Glu Arg Phe Ala Val Asn Pro
                35                  40                  45
Gly Leu Leu Glu Thr Ser Asp Gly Cys Arg Gln Ile Leu Gly Gln Leu
    50                  55                  60
Gln Pro Ser Leu Gln Thr Gly Ser Glu Glu Leu Arg Ser Leu Tyr Asn
65                  70                  75                  80
Thr Val Ala Thr Leu Tyr Cys Val His Gln Arg Ile Glu Val Lys Asp
                85                  90                  95
Thr Lys Glu Ala Leu Glu Asn Ile Glu Glu Glu Gln Asn Lys Ser Lys
                100                 105                 110
Lys Lys Ala Gln Pro Ala Asp Asp Thr Gly Asn Ser Ser Gln Val Ser
                115                 120                 125
Gln Asn Tyr Pro Val Val Gln Asn Leu Gln Gly Gln Met Val His Gln
            130                 135                 140
Pro Ile Ser Pro Arg Thr Leu Asn Ala Trp Val Lys Val Val Glu Glu
145                 150                 155                 160
Lys Ala Phe Ser Pro Glu Val Ile Pro Met Phe Thr Ala Leu Ser Glu
                165                 170                 175
Gly Ala Thr Pro Gln Asp Leu Asn Thr Met Leu Asn Thr Val Gly Gly
                180                 185                 190
His Gln Ala Ala Met Gln Met Leu Lys Glu Thr Ile Asn Glu Glu Ala
                195                 200                 205
Ala Glu Trp Asp Arg Leu His Pro Val His Ala Gly Pro Ile Ala Pro
    210                 215                 220
Asp Gln Met Arg Glu Pro Arg Gly Ser Asp Ile Ala Gly Ile Thr Ser
225                 230                 235                 240
Thr Leu Gln Glu Gln Ile Gly Trp Met Thr Asn Asn Pro Pro Ile Pro
                245                 250                 255
Val Gly Glu Ile Tyr Lys Arg Trp Ile Ile Leu Gly Leu Asn Lys Ile
                260                 265                 270
Val Arg Met Tyr Ser Pro Thr Ser Ile Leu Asp Ile Arg Gln Gly Pro
                275                 280                 285
Lys Glu Pro Phe Arg Asp Tyr Val Asp Arg Phe Tyr Lys Thr Leu Arg
                290                 295                 300
Ala Glu Gln Ala Ser Gln Asp Val Lys Asn Trp Met Thr Glu Thr Leu
305                 310                 315                 320
Leu Val Gln Asn Ala Asn Pro Asp Cys Lys Thr Ile Leu Lys Ala Leu
                325                 330                 335
Gly Pro Ala Ala Thr Leu Glu Glu Met Met Thr Ala Cys Gln Gly Val
                340                 345                 350
Gly Gly Pro Gly His Lys Ala Arg Val Leu Ala Glu Ala Met Ser Gln
                355                 360                 365
Val Thr Asn Ser Ala Thr Ile Met Met Gln Arg Gly Asn Phe Arg Asn
                370                 375                 380
Gln Arg Lys Ile Val Lys Cys Phe Asn Cys Gly Lys Glu Gly His Ile
385                 390                 395                 400
Thr Lys Asn Cys Arg Ala Pro Arg Lys Lys Gly Cys Trp Lys Cys Gly
                405                 410                 415
Lys Glu Gly His Gln Met Lys Asp Cys Thr Glu Arg Gln Ala Asn Phe
                420                 425                 430
```

-continued

Leu Gly Lys Ile Trp Pro Ser Lys Lys Gly Arg Pro Gly Asn Phe Leu
        435                 440                 445

Gln Ser Arg Pro Glu Pro Thr Ala Pro Pro Ala Glu Ser Phe Arg Phe
    450                 455                 460

Gly Glu Glu Thr Thr Thr Pro Ser Gln Lys Gln Glu Pro Thr Asp Lys
465                 470                 475                 480

Glu Leu Tyr Pro Leu Ala Ser Leu Arg Ser Leu Phe Gly Asn Asp Pro
                485                 490                 495

Ser Ser Gln

<210> SEQ ID NO 3
<211> LENGTH: 2545
<212> TYPE: DNA
<213> ORGANISM: Human immunodeficiency virus type 1

<400> SEQUENCE: 3

```
atgagagtga aggggatcag aagagctttt cagtacttgt ggagatgggg catcatgctc      60
cttgggatgt tgatgatctg tagtgctaca gaaaaattgt gggtcacagt ctattatggg     120
gtacctgtgt ggaaagaagc aaccaccact ctattttgtg catcagatgc taaagcatat     180
gatacagagg tacataatgt ttgggccaca catgcctgtg tacccacaga ccccagccca     240
caagaagtag aattgcaaaa tgtgacagaa gatttttaaca tgtggaaaaa taacatggta     300
gaacagatgc atgaggatgt aatcagtcta tgggatcaaa gcctaaagcc atgtgtaaaa     360
ttaaccccac tctgtgtcac tttaaattgc actgatttaa agaatgctac taataccact     420
agtagtagtg ggggaggaac gatggagaga ggagaaataa aaaactgctc tttcaaaatc     480
accacaaaca taagaaataa gatgcagaaa gaatatgcac tttttgataa acatgatgta     540
gtaccaatag ataaaaagaa tactagatat aggttgataa gttgtaacac ctcagtcatt     600
acacaggcct gtccaaaggt atcctttgag ccaattccca tacattttg tgccccggcc     660
ggttttgcga ttctaaagtg taaggataag aagttcaatg gaaagggatc atgtacaaaa     720
gtcagcacag tacaatgtac gcatggaatt aggccagtag tatcaactca actgctgtta     780
aatggcagtc tagcagaaga gaggtagta attagatctg acaatttcac agacaatgct     840
aaaaccataa tagtacagct gaatgaaact gtagaaatta ttgtacaag acccaacaac     900
aatacaagga aacgtataac tatgggacca gggagagtat tttatacaac aggagaaata     960
ataggagata taagacgagc acattgtaac attagtggaa caaatggaa taacacttta    1020
aaacagatag ttacaaaatt aagagaaaaa tttgggaata aaacaatagt ctttaagcaa    1080
tcctcaggag gggacccaga aattgtaatg cacactttta attgtggagg gaatttttc    1140
tactgtaaca caaacaact gtttaatagt acttggaatg atactgatac tctgaataat    1200
actgaaaggt caagtaaaac catcacgctc ccatgcagaa taaacaaat tataaacatg    1260
tggcaggaag taggaaaagc aatgtatgcc cctcccatca gcggacaaat tagatgttca    1320
tcaaatatta cagggcttct attagtaaga gatggtggta ataatgctga gaacgagacc    1380
gagatcctca gacctggagg aggaaacatg agggacaatt ggagaagtga attatataaa    1440
tataaagtag taaaaattga accattagga gtagcacccca ccaaggcaaa gagaagagtg    1500
gtgcagagag aaaaaagagc agtgggaacg ctaggagctt tgttccttgg gttcttggga    1560
acagcaggaa gcactatggg cgcagcgtca atgcgctga cggtacaggc cagacaatta    1620
ttgtctggta tagtgcaaca gcagaacaat ttgctgaggg ctattgaggc gcaacagcat    1680
```

| | |
|---|---|
| ttgttgcaac tcacagtctg gggcatcaag cagctccagg caagagtcct ggctgtggaa | 1740 |
| agatacctaa aggatcaaca gctcctaggg atttggggtt gctcgggaaa attcatttgc | 1800 |
| accactgctg tgccttggaa tgctagttgg agtaataaat ctctggataa gatttggaat | 1860 |
| aacatgacct ggatgcagtg ggaaagagaa attgacaatt acacagacct aatatacacc | 1920 |
| ttaattgaag aatcgcaaaa ccaacaagaa aagaatgaac aagaattatt ggaattagat | 1980 |
| aagtgggcaa gtttgtggaa ttggtttgac ataacaaaat ggctgtggta tataaaaata | 2040 |
| ttcataatga tagtaggagg cttggtaggt ttaagaatag ttttgctgt agtttctata | 2100 |
| gtgaatagag ttaggcaggg atactcacca ttatcatttc agacccactt cccagccccg | 2160 |
| aggggacccg acaggcccga aggaatcgaa gaagaaggtg gagacagaga cagagacaga | 2220 |
| tccattcgct tagtggatgg attcttagca ctcttctggg acgacctacg gagcctgtgc | 2280 |
| ctctccagct accaccgctt gagagactta ctcttgattg taacgaggat tgtggaactt | 2340 |
| ctgggacgca gggggtggga agccctcaaa tattggtgga atctcctgca gtattggagt | 2400 |
| caggaactaa agaatagtgc tattagcttg ctcaatacca cagctatagc agtagctgag | 2460 |
| gggacagata gggttataga aatagtacaa agagcttata gagctgttat ccacatacct | 2520 |
| agaagaataa gacagggctt tgaaa | 2545 |

```
<210> SEQ ID NO 4
<211> LENGTH: 1605
<212> TYPE: DNA
<213> ORGANISM: Human immunodeficiency virus type 1

<400> SEQUENCE: 4
```

| | |
|---|---|
| atgggtgcga gagcgtcagt attaagcggg ggagaattag ataaatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagacggctg tagacaaata | 180 |
| ctgggacagc tacaaccatc ccttcagaca ggatcagaag aacttagatc attatataat | 240 |
| acagtagcaa ccctctattg tgtgcatcaa aggatagagg taaaagacac caaggaagct | 300 |
| ttagagaata taggaggaga gcaaaacaaa agcaagaaaa agcacagcc agcagatgac | 360 |
| acaggaaaca gcagccaagt cagccaaaat taccctgtag tgcagaacct ccaggggcaa | 420 |
| atggtacatc agcccatatc acctagaact ttaaatgcat gggtaaaggt agtagaagag | 480 |
| aaggctttca gcccagaagt aatacccatg tttacagcat tatcagaagg agccaccccca | 540 |
| caagatttaa acaccatgct aaacacagtg gggggacatc aagcagccat gcaaatgtta | 600 |
| aaagagacca tcaatgagga agctgcagaa tgggatagat tgcatccagt gcatgcaggg | 660 |
| cctattgcac cagaccagat gagagaacca aggggaagtg acatagcagg aattactagt | 720 |
| acccttcagg aacaaatagg atggatgaca aataatccac ctatcccagt aggagaaatc | 780 |
| tataaaagat ggataatcct gggattaaat aaaatagtaa gaatgtatag ccctaccagc | 840 |
| attctggaca taagacaagg accaaaggaa ccctttagag actatgtaga ccggttctat | 900 |
| aaaactctaa gagccgagca agcttcacag gatgtaaaaa attggatgac agaaaccttg | 960 |
| ttggtccaaa atgcaaaccc agattgtaag actattttaa aagcattggg accagcagct | 1020 |
| acactagaag aaatgatgac agcatgtcag ggagtggggg acccggaca taagcaaga | 1080 |
| gttttggctg aagcaatgag ccaagtaaca aattccgcca ccataatgat gcaaagaggc | 1140 |
| aattttagga accaaagaaa gattgttaag tgtttcaatt gtggcaaaga agggcacata | 1200 |
| accaaaaatt gcagggcccc taggaaaaag gctgttggaa atgtggaaa ggaaggacac | 1260 |

-continued

```
caaatgaaag attgtactga gagacaggct aatttttag ggaagatctg gccttccaag    1320
aaggggaggc cagggaattt tcttcagagc agaccagagc caacagcccc accagcagag    1380
agcttcaggt ttggggagga gacaacaact ccctctcaga agcaggagcc gacagacaag    1440
gaactgtatc ccttagcttc cctcagatca ctctttggca acgacccctc gtcacaataa    1500 aggtagggg gcaactaaag gaagctctat tagatacagg agcagatgat aagggcgaat    1560
tccagcacac tggcggccgt tactagtgga tccgagctcg gtacc                    1605
```

<210> SEQ ID NO 5
<211> LENGTH: 856
<212> TYPE: PRT
<213> ORGANISM: Human immunodeficiency virus type 1

<400> SEQUENCE: 5

```
Met Arg Val Lys Glu Lys Tyr Gln His Leu Arg Arg Trp Gly Trp Arg
1               5                  10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Gly Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys His Asp Ile Ile Pro Ile Asp Asn Asp Thr Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Ala Glu Glu Val Val Ile
            260                 265                 270

Arg Ser Ala Asn Leu Thr Asp Asn Val Lys Thr Ile Ile Val Gln Leu
        275                 280                 285

Asn Gln Ser Val Glu Ile Asn Cys Thr Arg Pro Asn Asn Asn Thr Arg
    290                 295                 300

Lys Arg Ile Arg Ile Gln Arg Gly Pro Gly Arg Thr Phe Val Thr Ile
```

```
             305                 310                 315                 320
        Gly Lys Ile Gly Asn Met Arg Gln Ala His Cys Asn Ile Ser Arg Ala
                        325                 330                 335
        Lys Trp Asn Asn Thr Leu Lys Gln Ile Ala Ser Lys Leu Arg Glu Gln
                        340                 345                 350
        Tyr Gly Asn Asn Lys Thr Ile Ile Phe Lys Gln Ser Ser Gly Gly Asp
                        355                 360                 365
        Leu Glu Ile Val Thr His Ser Phe Asn Cys Gly Gly Glu Phe Phe Tyr
                370                 375                 380
        Cys Asn Ser Thr Gln Leu Phe Asn Ser Thr Trp Phe Asn Ser Thr Trp
        385                 390                 395                 400
        Ser Thr Glu Gly Ser Asn Asn Thr Glu Gly Ser Asp Thr Ile Thr Leu
                        405                 410                 415
        Pro Cys Arg Ile Lys Gln Ile Ile Asn Met Trp Gln Glu Val Gly Lys
                        420                 425                 430
        Ala Met Tyr Ala Pro Pro Ile Ser Gly Gln Ile Arg Cys Ser Ser Asn
                        435                 440                 445
        Ile Thr Gly Leu Leu Leu Thr Arg Asp Gly Gly Asn Asn Asn Asn Gly
                        450                 455                 460
        Ser Glu Ile Phe Arg Pro Gly Gly Gly Asp Met Arg Asp Asn Trp Arg
        465                 470                 475                 480
        Ser Glu Leu Tyr Lys Tyr Lys Val Val Lys Ile Glu Pro Leu Gly Val
                        485                 490                 495
        Ala Pro Thr Lys Ala Lys Arg Arg Val Val Gln Arg Glu Lys Arg Ala
                        500                 505                 510
        Val Gly Ile Gly Ala Leu Phe Leu Gly Phe Leu Gly Ala Ala Gly Ser
                        515                 520                 525
        Thr Met Gly Ala Ala Ser Met Thr Leu Thr Val Gln Ala Arg Gln Leu
                530                 535                 540
        Leu Ser Gly Ile Val Gln Gln Gln Asn Asn Leu Leu Arg Ala Ile Glu
        545                 550                 555                 560
        Ala Gln Gln His Leu Leu Gln Leu Thr Val Trp Gly Ile Lys Gln Leu
                        565                 570                 575
        Gln Ala Arg Ile Leu Ala Val Glu Arg Tyr Leu Lys Asp Gln Gln Leu
                        580                 585                 590
        Leu Gly Ile Trp Gly Cys Ser Gly Lys Leu Ile Cys Thr Thr Ala Val
                        595                 600                 605
        Pro Trp Asn Ala Ser Trp Ser Asn Lys Ser Leu Glu Gln Ile Trp Asn
                610                 615                 620
        His Thr Thr Trp Met Glu Trp Asp Arg Glu Ile Asn Asn Tyr Thr Ser
        625                 630                 635                 640
        Leu Ile His Ser Leu Ile Glu Glu Ser Gln Asn Gln Gln Glu Lys Asn
                        645                 650                 655
        Glu Gln Glu Leu Leu Glu Leu Asp Lys Trp Ala Ser Leu Trp Asn Trp
                        660                 665                 670
        Phe Asn Ile Thr Asn Trp Leu Trp Tyr Ile Lys Ile Phe Ile Met Ile
                        675                 680                 685
        Val Gly Gly Leu Val Gly Leu Arg Ile Val Phe Ala Val Leu Ser Ile
                690                 695                 700
        Val Asn Arg Val Arg Gln Gly His Ser Pro Leu Ser Phe Gln Thr His
        705                 710                 715                 720
        Leu Pro Thr Pro Gly Gly Pro Asp Arg Pro Glu Gly Ile Glu Glu Glu
                        725                 730                 735
```

```
Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
            770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
            835                 840                 845

Gln Gly Leu Glu Arg Ile Leu Leu
            850                 855

<210> SEQ ID NO 6
<211> LENGTH: 500
<212> TYPE: PRT
<213> ORGANISM: Human immunodeficiency virus type 1

<400> SEQUENCE: 6

Met Gly Ala Arg Ala Ser Val Leu Ser Gly Gly Lys Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Cys Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Lys Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
```

```
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
        275                 280                 285
Pro Lys Glu Pro Phe Arg Asp Tyr Val Asp Arg Phe Tyr Lys Thr Leu
    290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
            325                 330                 335
Leu Gly Pro Ala Ala Thr Leu Glu Glu Met Met Thr Ala Cys Gln Gly
        340                 345                 350
Val Gly Gly Pro Gly His Lys Ala Arg Val Leu Ala Glu Ala Met Ser
    355                 360                 365
Gln Val Thr Asn Ser Ala Thr Ile Met Met Gln Arg Gly Asn Phe Arg
370                 375                 380
Asn Gln Arg Lys Ile Val Lys Cys Phe Asn Cys Gly Lys Glu Gly His
385                 390                 395                 400
Ile Ala Arg Asn Cys Arg Ala Pro Arg Lys Lys Gly Cys Trp Lys Cys
            405                 410                 415
Gly Lys Glu Gly His Gln Met Lys Asp Cys Thr Glu Arg Gln Ala Asn
        420                 425                 430
Phe Leu Gly Lys Ile Trp Pro Ser Tyr Lys Gly Arg Pro Gly Asn Phe
    435                 440                 445
Leu Gln Ser Arg Pro Glu Pro Thr Ala Pro Glu Glu Ser Phe Arg
450                 455                 460
Ser Gly Val Glu Thr Thr Thr Pro Pro Gln Lys Gln Glu Pro Ile Asp
465                 470                 475                 480
Lys Glu Leu Tyr Pro Leu Thr Ser Leu Arg Ser Leu Phe Gly Asn Asp
            485                 490                 495
Pro Ser Ser Gln
            500

<210> SEQ ID NO 7
<211> LENGTH: 2571
<212> TYPE: DNA
<213> ORGANISM: Human immunodeficiency virus type 1

<400> SEQUENCE: 7
atgagagtga aggagaaaata tcagcacttg cggagatggg ggtggagatg gggcaccatg    60
ctccttggga tgttgatgat ttgtagtgct acagaaaaat tgtgggtcac agtctattat   120
ggggtacctg tgtggaagga agcaaccacc actctatttt gtgcatcaga tgctaaagca   180
tatgatacag aggtacataa tgtttgggcc acacatgcct gtgtacccac agaccccaac   240
ccacaagaag tagtattggt aaatgtgaca gaaaatttta acatgtggaa aatgatatg   300
gtagaacaga tgcatgagga tataatcagt ttatgggatc aaagcctaaa gccatgtgta   360
aaattaaccc cactctgtgt tagttttaaag tgcactgatt tgaagaatga tactaatacc   420
aatagtagta gcgggggaat gataatggag aaaggagaga taaaaaactg ctctttcaat   480
atcagcacaa gcataagagg taaggtgcag aaagaatatg cattttttta taaacatgat   540
ataataccaa tagataatga tactaccagc tatacgttga caagttgtaa cacctcagtc   600
attacacagg cctgtccaaa ggtatccttt gagccaattc ccatacatta ttgtgccccg   660
```

```
gctggttttg cgattctaaa atgtaataat aagacgttca atggaacagg accatgtaca    720
aatgtcagca cagtacaatg tacacatgga attaagccag tagtatcaac tcaactgctg    780
ttaaatggca gtctagcaga agaagaggta gtaattagat ctgccaatct cacagacaat    840
gttaaaacca taatagtaca gctgaaccaa tctgtagaaa ttaattgtac aagacccaac    900
aacaatacaa gaaaaagaat ccgtatccag agaggaccag ggagaacatt tgttacaata    960
ggaaaaatag gaaatatgag acaagcacat tgtaacatta gtagagcaaa atggaataac   1020
actttaaaac agatagctag caaattaaga gaacaatatg gaataataaa acaataatc    1080 tttaagcagt cctcaggagg ggacctagaa attgtaacgc acagttttaa ttgtggaggg   1140
gaatttttct actgtaattc aacacaactg tttaatagta cttggtttaa tagtacttgg   1200
agtactgaag ggtcaaataa cactgaagga agtgacacaa tcacactccc atgcagaata   1260
aaacaaatta taaacatgtg gcaggaagta ggaaaagcaa tgtatgcccc tcccatcagc   1320
ggacaaatta gatgttcatc aaatattaca gggctgctat taacaagaga tggtggtaat   1380
aacaacaatg ggtccgagat cttcagacct ggaggaggag atatgaggga caattggaga   1440
agtgaattat ataaatataa agtagtaaaa attgaaccat taggagtagc acccaccaag   1500
gcaaagagaa gagtggtgca gagagaaaaa agagcagtgg gaataggagc tttgttcctt   1560
gggttcttgg gagcagcagg aagcactatg ggcgcagcgt caatgacgct gacggtacag   1620
gccagacaat tattgtctgg tatagtgcag cagcagaaca atttgctgag ggctattgag   1680
gcgcaacagc atctgttgca actcacagta tggggcatca agcagctcca ggcaagaatc   1740
ctggctgtgg aaagatacct aaaggatcaa cagctcctgg ggatttgggg ttgctctgga   1800
aaactcattt gcaccactgc tgtgccttgg aatgctagtt ggagtaataa atctctggaa   1860
cagatttgga atcacacgac ctggatggag tgggacagag aaattaacaa ttacacaagc   1920
ttaatacact ccttaattga agaatcgcaa aaccaacaag aaaagaatga acaagaatta   1980
ttggaattag ataaatgggc aagtttgtgg aattggttta acataacaaa ttggctgtgg   2040
tatataaaaa tattcataat gatagtagga ggcttggtag gtttaagaat agttttttgct   2100 gtactttcta tagtgaatag agttaggcag ggacattcac cattatcgtt tcagacccac   2160
ctcccaaccc cggggggacc cgacaggccc gaaggaatag aagaagaagg tggagagaga   2220
gacagagaca gatccattcg attagtgaac ggatccttag cacttatctg ggacgatctg   2280
cgaagcctgt gcctcttcag ctaccaccgc ttgagagact tactcttgat tgtaacgagg   2340
attgtggaac ttctgggacg caggggtgg gaagccctca aatattggtg gaatctccta   2400
cagtattgga gtcaggaact aaagaatagt gctgttagct tgctcaatgc cacagccata   2460
gcagtagctg aggggacaga tagggttata gaagtagtac aaggagcttg tagagctatt   2520
cgccacatac ctagaagaat aagacagggc ttggaaagga ttttgctata a            2571

<210> SEQ ID NO 8
<211> LENGTH: 1503
<212> TYPE: DNA
<213> ORGANISM: Human immunodeficiency virus type 1

<400> SEQUENCE: 8
atgggtgcga gagcgtcagt attaagcggg ggaaaattag atcgatggga aaaaattcgg     60
ttaaggccag ggggaaagaa aaaatataaa ttaaaacata tagtatgggc aagcagggag    120
ctagaacgat tcgcagttaa tcctggcctg ttagaaacat cagaaggctg tagacaaata    180
```

-continued

```
ctgggacagc tacaaccatc ccttcagaca ggatcagaag aatgtagatc attatataat    240
acagtagcaa ccctctattg tgtgcatcaa aggatagaga taaagacac caaggaagct    300 ttagacaaga taaaggaaga gcaaaacaaa agtaagaaaa agcacagca agcagcagct    360 gacacaggac acagcagtca ggtcagccaa aattacccta tagtgcagaa catccagggg    420
caaatggtac atcaggccat atcacctaga actttaaatg catgggtaaa agtagtagaa    480
gagaaggctt tcagcccaga agtaataccc atgttttcag cattatcaga aggagccacc    540
ccacaagatt taaacaccat gctaaacaca gtggggggac atcaagcagc catgcaaatg    600
ttaaaagaga ccatcaatga ggaagctgca gaatgggata gagtgcatcc agtgcatgca    660
gggcctatcg caccaggcca gatgagagaa ccaaggggaa gtgacatagc aggaactact    720
agtacccttc aggaacaaat aggatggatg acaaataatc cacctatccc agtaggagaa    780
atttataaaa gatggataat cctgggatta aataagatag taagaatgta tagccctacc    840
agcattctgg acataagaca aggaccaaaa gaacctttta gagactatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagca   1020
gctacactag aagaaatgat gacagcatgt cagggagtgg gaggacccgg ccataaggca   1080
agagttttgg ctgaagcaat gagccaagta acaaattcag ctaccataat gatgcagaga   1140
ggcaatttta ggaaccaaag aaagattgtt aagtgtttca attgtggcaa agaagggcac   1200
atagccagaa attgcagggc ccctaggaaa aagggctgtt ggaaatgtgg aaaggaagga   1260
caccaaatga aagattgtac tgagagacag gctaattttt tagggaagat ctggccttcc   1320
tacaagggaa ggccagggaa ttttcttcag agcagaccag agccaacagc cccaccagaa   1380
gagagcttca ggtctggggt agagacaaca actccccctc agaagcagga gccgatagac   1440
aaggaactgt atcctttaac ttccctcaga tcactctttg gcaacgaccc ctcgtcacaa   1500
taa                                                                  1503
```

<210> SEQ ID NO 9
<211> LENGTH: 10
<212> TYPE: PRT
<213> ORGANISM: Human immunodeficiency virus type 1

<400> SEQUENCE: 9

Ser Pro Arg Thr Leu Asn Ala Trp Val Lys
1               5                   10

<210> SEQ ID NO 10
<211> LENGTH: 10
<212> TYPE: PRT
<213> ORGANISM: Human immunodeficiency virus type 1

<400> SEQUENCE: 10

Leu Ser Glu Gly Ala Thr Pro Gln Asp Leu
1               5                   10

<210> SEQ ID NO 11
<211> LENGTH: 11
<212> TYPE: PRT
<213> ORGANISM: Human immunodeficiency virus type 1

<400> SEQUENCE: 11

Asn Glu Glu Ala Ala Glu Trp Asp Arg Leu His
1               5                   10

<210> SEQ ID NO 12
<211> LENGTH: 10
<212> TYPE: PRT
<213> ORGANISM: Human immunodeficiency virus type 1

<400> SEQUENCE: 12

Lys Arg Trp Ile Ile Leu Gly Leu Asn Lys
1               5                   10

<210> SEQ ID NO 13
<211> LENGTH: 9
<212> TYPE: PRT
<213> ORGANISM: Human immunodeficiency virus type 1

<400> SEQUENCE: 13

Ile Leu Asp Ile Arg Gln Gly Pro Lys
1               5

<210> SEQ ID NO 14
<211> LENGTH: 10
<212> TYPE: PRT
<213> ORGANISM: Human immunodeficiency virus type 1

<400> SEQUENCE: 14

Asp Tyr Val Asp Arg Phe Tyr Lys Thr Leu
1               5                   10

<210> SEQ ID NO 15
<211> LENGTH: 9
<212> TYPE: PRT
<213> ORGANISM: Human immunodeficiency virus type 1

<400> SEQUENCE: 15

Val Gln Asn Ala Asn Pro Asp Cys Lys
1               5

<210> SEQ ID NO 16
<211> LENGTH: 10
<212> TYPE: PRT
<213> ORGANISM: Human immunodeficiency virus type 1

<400> SEQUENCE: 16

Ala Cys Gln Gly Val Gly Gly Pro Gly His
1               5                   10

<210> SEQ ID NO 17
<211> LENGTH: 11
<212> TYPE: PRT
<213> ORGANISM: Human immunodeficiency virus type 1

<400> SEQUENCE: 17

Val Gly Gly Pro Gly His Lys Ala Arg Val Leu
1               5                   10

<210> SEQ ID NO 18
<211> LENGTH: 11
<212> TYPE: PRT
<213> ORGANISM: Feline immunodeficiency virus

<400> SEQUENCE: 18

Asp Pro Lys Met Val Ser Ile Phe Met Glu Lys
1               5                   10

<210> SEQ ID NO 19

```
<211> LENGTH: 10
<212> TYPE: PRT
<213> ORGANISM: Feline immunodeficiency virus

<400> SEQUENCE: 19

Phe Ser Ala Asn Leu Thr Pro Thr Asp Met
1               5                   10

<210> SEQ ID NO 20
<211> LENGTH: 11
<212> TYPE: PRT
<213> ORGANISM: Feline immunodeficiency virus

<400> SEQUENCE: 20

Lys Gln Met Thr Ala Glu Tyr Asp Arg Thr His
1               5                   10

<210> SEQ ID NO 21
<211> LENGTH: 10
<212> TYPE: PRT
<213> ORGANISM: Feline immunodeficiency virus

<400> SEQUENCE: 21

Arg Ala Trp Tyr Leu Glu Ala Leu Ser Lys
1               5                   10

<210> SEQ ID NO 22
<211> LENGTH: 9
<212> TYPE: PRT
<213> ORGANISM: Feline immunodeficiency virus

<400> SEQUENCE: 22

Ala Val Gln Met Lys Gln Gly Val Lys
1               5

<210> SEQ ID NO 23
<211> LENGTH: 10
<212> TYPE: PRT
<213> ORGANISM: Feline immunodeficiency virus

<400> SEQUENCE: 23

Ser Phe Ile Asp Arg Leu Phe Ala Gln Ile
1               5                   10

<210> SEQ ID NO 24
<211> LENGTH: 9
<212> TYPE: PRT
<213> ORGANISM: Feline immunodeficiency virus

<400> SEQUENCE: 24

Ile Ala Asn Ala Asn Pro Asp Cys Lys
1               5

<210> SEQ ID NO 25
<211> LENGTH: 10
<212> TYPE: PRT
<213> ORGANISM: Feline immunodeficiency virus

<400> SEQUENCE: 25

Ala Cys Gln Glu Val Gly Ser Pro Gly Tyr
1               5                   10

<210> SEQ ID NO 26
<211> LENGTH: 11
<212> TYPE: PRT
```

```
<213> ORGANISM: Feline immunodeficiency virus

<400> SEQUENCE: 26

Val Gly Ser Pro Gly Tyr Lys Met Gln Leu Leu
1               5                   10

<210> SEQ ID NO 27
<211> LENGTH: 30
<212> TYPE: PRT
<213> ORGANISM: Feline immunodeficiency virus

<400> SEQUENCE: 27

Pro Ile Gln Thr Val Asn Gly Ala Pro Gln Tyr Val Ala Leu Asp Pro
1               5                   10                  15

Lys Met Val Ser Ile Phe Met Glu Lys Ala Arg Glu Gly Leu
            20                  25                  30

<210> SEQ ID NO 28
<211> LENGTH: 28
<212> TYPE: PRT
<213> ORGANISM: Feline immunodeficiency virus

<400> SEQUENCE: 28

Gln Tyr Val Ala Leu Asp Pro Lys Met Val Ser Ile Phe Met Glu Lys
1               5                   10                  15

Ala Arg Glu Gly Leu Gly Gly Glu Glu Val Gln Leu
            20                  25

<210> SEQ ID NO 29
<211> LENGTH: 26
<212> TYPE: PRT
<213> ORGANISM: Feline immunodeficiency virus

<400> SEQUENCE: 29

Glu Val Gln Leu Trp Phe Thr Ala Phe Ser Ala Asn Leu Thr Pro Thr
1               5                   10                  15

Asp Met Ala Thr Leu Ile Met Ala Ala Pro
            20                  25

<210> SEQ ID NO 30
<211> LENGTH: 29
<212> TYPE: PRT
<213> ORGANISM: Feline immunodeficiency virus

<400> SEQUENCE: 30

Thr Leu Ile Met Ala Ala Pro Gly Cys Ala Ala Asp Lys Glu Ile Leu
1               5                   10                  15

Asp Glu Ser Leu Lys Gln Leu Thr Ala Glu Tyr Asp Arg
            20                  25

<210> SEQ ID NO 31
<211> LENGTH: 30
<212> TYPE: PRT
<213> ORGANISM: Feline immunodeficiency virus

<400> SEQUENCE: 31

Ser Leu Lys Gln Leu Thr Ala Glu Tyr Asp Arg Thr His Pro Pro Asp
1               5                   10                  15

Gly Pro Arg Pro Leu Pro Tyr Phe Thr Ala Ala Glu Ile Met
            20                  25                  30

<210> SEQ ID NO 32
```

```
<211> LENGTH: 30
<212> TYPE: PRT
<213> ORGANISM: Feline immunodeficiency virus

<400> SEQUENCE: 32

Pro Leu Pro Tyr Phe Thr Ala Ala Glu Ile Met Gly Ile Gly Leu Thr
1               5                   10                  15

Gln Glu Gln Gln Ala Glu Ala Arg Phe Ala Pro Ala Arg Met
            20                  25                  30

<210> SEQ ID NO 33
<211> LENGTH: 30
<212> TYPE: PRT
<213> ORGANISM: Feline immunodeficiency virus

<400> SEQUENCE: 33

Glu Gln Gln Ala Glu Ala Arg Phe Ala Pro Ala Arg Met Gln Cys Arg
1               5                   10                  15

Ala Trp Tyr Leu Glu Ala Leu Gly Lys Leu Ala Ala Ile Lys
            20                  25                  30

<210> SEQ ID NO 34
<211> LENGTH: 28
<212> TYPE: PRT
<213> ORGANISM: Feline immunodeficiency virus

<400> SEQUENCE: 34

Leu Glu Ala Leu Gly Lys Leu Ala Ala Ile Lys Ala Lys Ser Pro Arg
1               5                   10                  15

Ala Val Gln Leu Arg Gln Gly Ala Lys Glu Asp Tyr
            20                  25

<210> SEQ ID NO 35
<211> LENGTH: 29
<212> TYPE: PRT
<213> ORGANISM: Feline immunodeficiency virus

<400> SEQUENCE: 35

Val Gln Leu Arg Gln Gly Ala Lys Glu Asp Tyr Ser Ser Phe Ile Asp
1               5                   10                  15

Arg Leu Phe Ala Gln Ile Asp Gln Glu Gln Asn Thr Ala
            20                  25

<210> SEQ ID NO 36
<211> LENGTH: 28
<212> TYPE: PRT
<213> ORGANISM: Feline immunodeficiency virus

<400> SEQUENCE: 36

Phe Ala Gln Ile Asp Gln Glu Gln Asn Thr Ala Glu Val Lys Leu Tyr
1               5                   10                  15

Leu Lys Gln Ser Leu Ser Ile Ala Asn Ala Asn Ala
            20                  25

<210> SEQ ID NO 37
<211> LENGTH: 30
<212> TYPE: PRT
<213> ORGANISM: Feline immunodeficiency virus

<400> SEQUENCE: 37

Lys Gln Ser Leu Ser Ile Ala Asn Ala Asn Ala Glu Cys Lys Lys Ala
1               5                   10                  15
```

```
Met Ser His Leu Lys Pro Glu Ser Thr Leu Glu Glu Lys Leu
            20                  25                  30
```

<210> SEQ ID NO 38
<211> LENGTH: 27
<212> TYPE: PRT
<213> ORGANISM: Feline immunodeficiency virus

<400> SEQUENCE: 38

```
Leu Lys Pro Glu Ser Thr Leu Glu Glu Lys Leu Arg Ala Cys Gln Glu
1               5                   10                  15

Val Gly Ser Pro Gly Tyr Lys Met Gln Leu Leu
            20                  25
```

<210> SEQ ID NO 39
<211> LENGTH: 15
<212> TYPE: PRT
<213> ORGANISM: Human immunodeficiency virus type 1

<400> SEQUENCE: 39

```
Gln Gly Pro Lys Glu Pro Phe Arg Asp Tyr Val Asp Arg Phe Tyr
1               5                   10                  15
```

<210> SEQ ID NO 40
<211> LENGTH: 15
<212> TYPE: PRT
<213> ORGANISM: Feline immunodeficiency virus

<400> SEQUENCE: 40

```
Gln Gly Ala Lys Glu Asp Tyr Ser Ser Phe Ile Asp Arg Leu Phe
1               5                   10                  15
```

<210> SEQ ID NO 41
<211> LENGTH: 10
<212> TYPE: PRT
<213> ORGANISM: Feline immunodeficiency virus

<400> SEQUENCE: 41

```
Phe Ser Ala Asn Leu Thr Ser Thr Asp Met
1               5                   10
```

<210> SEQ ID NO 42
<211> LENGTH: 10
<212> TYPE: PRT
<213> ORGANISM: Feline immunodeficiency virus

<400> SEQUENCE: 42

```
Arg Ala Trp Tyr Leu Glu Ala Leu Gly Arg
1               5                   10
```

<210> SEQ ID NO 43
<211> LENGTH: 10
<212> TYPE: PRT
<213> ORGANISM: feline immunodeficiency virus

<400> SEQUENCE: 43

```
Arg Ala Trp Tyr Leu Glu Ala Leu Gly Lys
1               5                   10
```

<210> SEQ ID NO 44
<211> LENGTH: 9
<212> TYPE: PRT
<213> ORGANISM: feline immunodeficiency virus

<400> SEQUENCE: 44

```
Ala Val Gln Leu Arg Gln Gly Ala Lys
1               5

<210> SEQ ID NO 45
<211> LENGTH: 9
<212> TYPE: PRT
<213> ORGANISM: feline immunodeficiency virus

<400> SEQUENCE: 45

Ala Val Gln Leu Lys Gln Gly Ala Lys
1               5

<210> SEQ ID NO 46
<211> LENGTH: 9
<212> TYPE: PRT
<213> ORGANISM: feline immunodeficiency virus

<400> SEQUENCE: 46

Ile Ala Asn Ala Asn Ala Glu Cys Lys
1               5
```